(12) United States Patent
Vargeese et al.

(10) Patent No.: US 7,777,023 B2
(45) Date of Patent: Aug. 17, 2010

(54) METHOD FOR THE CHEMICAL SYNTHESIS OF OLIGONUCLEOTIDES

(75) Inventors: Chandra Vargeese, Broomfield, CO (US); Christopher Shaffer, Longmont, CO (US); Weimin Wang, Superior, CO (US)

(73) Assignee: Sirna Therapeutics, Inc., San Francisco, CA (US)

( * ) Notice: Subject to any disclaimer, the term of this patent is extended or adjusted under 35 U.S.C. 154(b) by 1242 days.

(21) Appl. No.: 11/251,407

(22) Filed: Oct. 14, 2005

(65) Prior Publication Data

US 2006/0036090 A1 Feb. 16, 2006

Related U.S. Application Data

(60) Division of application No. 09/887,182, filed on Jun. 22, 2001, now Pat. No. 6,995,259, which is a continuation-in-part of application No. 09/426,079, filed on Oct. 22, 1999, now abandoned, which is a continuation-in-part of application No. 09/178,154, filed on Oct. 23, 1998.

(51) Int. Cl.
*C07H 21/00* (2006.01)
*C07H 19/04* (2006.01)
*C12N 11/14* (2006.01)
*G01N 33/551* (2006.01)
*C07K 1/00* (2006.01)

(52) U.S. Cl. .................. 536/25.3; 536/26.7; 536/27.14; 435/176; 435/181; 435/524; 530/811; 556/413

(58) Field of Classification Search ................ 536/25.3, 536/26.7, 27.14; 435/176, 181, 524; 530/811; 556/413

See application file for complete search history.

(56) References Cited

U.S. PATENT DOCUMENTS

| | | | |
|---|---|---|---|
| 4,306,839 A | 12/1981 | Pien | |
| 4,458,066 A | 7/1984 | Caruthers et al. | |
| 4,923,901 A | 5/1990 | Koester et al. | |
| 4,973,679 A | 11/1990 | Caruthers et al. | |
| 4,987,071 A | 1/1991 | Cech et al. | |
| 5,002,884 A * | 3/1991 | Kobayashi et al. | 435/176 |
| 5,132,418 A | 7/1992 | Caruthers et al. | |
| 5,141,813 A * | 8/1992 | Nelson | 428/402 |
| 5,153,319 A | 10/1992 | Caruthers et al. | |
| 5,252,723 A | 10/1993 | Bhatt | |
| 5,281,701 A | 1/1994 | Winayak | |
| 5,334,711 A | 8/1994 | Sproat | |
| 5,419,966 A | 5/1995 | Reed | |
| 5,589,332 A | 12/1996 | Shih et al. | |
| 5,627,053 A | 5/1997 | Usman et al. | |
| 5,672,695 A | 9/1997 | Eckstein et al. | |
| 5,674,856 A | 10/1997 | Furukawa et al. | |
| 5,686,599 A | 11/1997 | Tracz | |
| 5,716,824 A | 2/1998 | Beigelman et al. | |
| 5,723,599 A | 3/1998 | Klem et al. | |
| 5,741,679 A | 4/1998 | George et al. | |
| 5,804,683 A | 9/1998 | Usman et al. | |
| 5,831,071 A | 11/1998 | Wincott et al. | |
| 5,834,186 A | 11/1998 | George et al. | |
| 5,849,902 A | 12/1998 | Arrow et al. | |
| 5,871,914 A | 2/1999 | Nathan et al. | |
| 5,989,912 A | 11/1999 | Arrow et al. | |

FOREIGN PATENT DOCUMENTS

| | | |
|---|---|---|
| DE | 280968 | 7/1983 |
| EP | 0 325 970 | 1/1989 |
| JP | 2169605 A | 12/1985 |
| WO | WO 91/03162 | 6/1990 |
| WO | WO 92/07065 | 9/1991 |
| WO | WO 93/15187 | 1/1993 |
| WO | WO 93/23569 | 4/1993 |
| WO | WO 93/23057 | 5/1993 |
| WO | WO 94/01446 | 6/1993 |
| WO | WO 94/02595 | 7/1993 |
| WO | WO 95/04818 | 8/1994 |
| WO | WO 95/13380 | 11/1994 |
| WO | WO 95/23225 | 2/1995 |
| WO | WO 97/42202 | 10/1996 |
| WO | WO 97/26270 | 12/1996 |
| WO | WO 98/13526 | 9/1997 |
| WO | WO 98/27104 | 12/1997 |
| WO | WO 98/28317 | 12/1997 |
| WO | WO 99/29842 | 12/1998 |
| WO | WO 99/54459 | 4/1999 |
| WO | WO 00/24931 | 10/1999 |
| WO | WO 00/26226 | 10/1999 |

OTHER PUBLICATIONS

Alui et al., *Nucl. AcidsIds Res.,*. 19:1527-1532 (1991).
Bartel et al., *Science* 261:1411-1418 (1993).
Bass, *Nature* 411:428-429 (2001).
Beaucage and Iyer, *Tetra.* 49:1925 (1993) Beigelman et al. J. Biol.. Chem. 270-25702 (1995).
Beaudry et al., *Science* 257:635-641 (1992).
Beigelman et al., *J. Biol. Chem..* 270:25702 (1995).
Birch-Hirschfeld et al. "A versatile support for the synthesis of oligonucleotides of extended length and scale," *Nucl. Acids Res,.* 22:1760-1761 (1994).
Breaker et al., *TIBTECH* 12:268 (1994).
Breaker, *Curr. Op. Biotech.* 7:442 (1996).
Brody and Gold, *J. Biotechnol.* 74:5 (2000).
Burgin et al., "Chemically Modified Hammerhead Ribozymes with Improved Catalytic Rates," *Biochem.* 35:214090-14097 (1996).
Burlina et al., *Bioorg. Med. Chem.* 5:1999-2010 (1997).

(Continued)

*Primary Examiner*—James O. Wilson
*Assistant Examiner*—Paul V. Ward

(57) ABSTRACT

The present invention features novel compositions, linkers, derivatized solid supports, and methods for the efficient solid phase synthesis of oligonucleotides, including RNA, DNA, RNA-DNA chimeras, and analogs thereof.

20 Claims, 11 Drawing Sheets

OTHER PUBLICATIONS

Caruthers et al., "Chemical Synthesis of Deoxyoligonucleotides and Deoxyoligonucleotide Analogs," in *Methods in Enzy.* 211:3-19 (1992) Usman and Cedergren Trends in Biochem. Sci. 17:334-339 (1992).
Cech et al., *JAMA* 260:3030 (1988).
Christoffersen and Marrr, *J. Med. Chem.* 38:2023-2037 (1995).
Christoffersen, *Nature Biotech.* 2:483-484 (1997).
Crooke, *Ad. Pharmacol.* 40:1-49 (1997).
Crooke, *Biotech. Genet. Eng. Rev.* 15:121-157 (1998).
Crooke, *Methods. Enzymol.* 313:3-45 (2000).
Delihas et al., *Nature* 15:751-753 (1997).
Dell-Aquila et al., *Tetra. Lett.* 38:5289-52923327-3330 (1997).
Dreyfuss, *Einstein Quart. J. Bio. Med.* 6:92 (1988).
Duval-Valentin et al., *Proc. Natl. Acad. Sci. USA* 89:504 (1992).
Earnshaw and Gait, *Biopoly.* (*Nucl. Acid. Sci.*) 48:39-55 (1998).
Egholm et al., *Nature* 365:566 (1993).
Elbashir et al., *Nature* 411:494-498 (2001).
Fox, *Curr. Med. Chem.* 7:17-37 (2000).
Gait et al., Chapter 2 in *Oligonucleotides and Analogues; A Practical Approach*, ed. By Eckstein, IRL Press, Oxford, pp. 25-48 (19191).
Gold et al., *Annu. Rev. Biochem.* 64:763 (1995).
Greenberg "Photochemical Release of Protected Oligonucleotides Containing 3'-Glycolate Termini," *Tetra.* 51:29-38 (1995).
Hammann et al., "Length Variation of Helix III in a Hammerhead Ribozyme and its Influence on Cleavage Activity," *Antisense & Nucl. Acid Drug Dev.* 9:25-31 (1999).
Haseloff and Gerlach, *Nature* 334:585 (1988).
Hermann and Patel, *Science*, 287:820 (2000).
Hovinen et al. "Novel Solid Supports for the Preparation of 3'-Derivatized Oligonucleotides: Introduction of 3'-Alkylphosphate Thether Groups Bearing Amino, Carboxy, Carboxamido, and Mercapto Functionalities," *Tetrahedron* 50:7203-7218 (1994).
Hunziker and Leumann, "Nucleic Acid Analogues: Synthesis and properties," in *Modern Synthetic Methods*, VCH 331:417 (1995).
Jayasena, *Clin. Chem.* 45:1628 (1999).
Jeffries et al., *Nucl. Acids Res.* 17:1371 (1989).
Joyce, *Gene* 82:83-87 (1989).
Joyce, *Scientific Amer.* 267:90-97 (1992).
Karpeisky et al., *Tetra. Lett.* 39:1131 (1998).
Katzhendler et al. "Spacer Effect of the Synthesis of Olgodeoxynucleotides by the Phosphite Method," *Reactive Polymers* 6:175-187 (1987).
Katzhendler et al. "The Effect of Spacer, Linkage and Solid Support on the Synthesis of Oligonucleotides," *Tetrahedron* 45:2777-2792 (1989).
Kim et al., *Proc. Natl. Acad. Sci. USA* 84:8788 (1987).
Kitamura et al., *Chem. Lett.* 10:1134-1135 (2000).
Kumar et al., *FASEB* 9:1183 (1995).
Kusser, *J. Biotechnol.* 74:27 (2000).
Limbach et al., "Summary: the modified nucleosides of RNA," in *Nucl. Acids Res.* 22:2183-2196 (1994).
Maskos and Southern, *Nucl. Acids Res.* 20:1679-1684 (1992).
Mesmaeker et al., "Novel Backbone Replacements for Oligonucleotides in Carobhydrate Modifications," in *Anti. Res. ACS*, 24:39 (1994)Karpeisky et al. Tetra. Lett. 39:1131 (1998).
Mitra et al., *Proc. Natl. Acad. Sci. USAa* 93:6780-6785 (1996).
Mukhopadhyay & Roth, *Crit. Re. in Oncogenesis* 7:151-190 (1996).
Nathans et al., *Ann. Rev. Biochem.* 44:273 (1975).
Orgel, *Proc. R. Soc. London*, B 205:435 (1979).
Palom et al., *Tetra. Lett.* 34:2195-2198 (1991).
Perrault et al., *Nature* 344:565 (1990).
Picken et al., *Science* 253:314 (1991).
Player and Torrence, *Pharmacol. Ther.* 78:55-113 (1998).
Pon & Yu, *Tetra Lett.* 38:33237-3330 (1997).
Pon et al. "Derivatization of Controlled Pore Glass Beads for Solid Phase Oligonucleotide Synthesis," *BioTech.* 6:768-775 (1988).
Pon et al., *Nucl. Acids Res.* 27:1531-1538 (1999).
Pon, Chapter 19—Solid-Phase Supports for Oligonucloetide Synthesis, in *Methods in Miol. Biol.*, vol. 20, *Protocols for Oligonucleotides and Analogs*, edited, by Agrawal, Humanan Press, Inc., Totowa, NJ, pp. 465-497 (1993).
Praseuth et al., *Biochem. Biophys. Acta.* 11489:181-206 (2000).
Santoro et al., *Proc. Natl. Acad. Sci.* 94:4262 (1997).
Scaringe et al., *Nucl. Acids. Res.* 18:5433-5441 (1990).
Schmajuk et al., *J. Biol. Chem.* 274:21783-21789 (1999).
Silverman et al., *Methods Enzymol.* 313:522-533 (1999).
Sproat et al. "An Efficient Method for the Isolation and Purification of Oligoribonucleotides," *Nucl. and Nucl.* 14:255-273 (1995).
Stein and Chen, *Science* 261:1004 (1993).
Stein et al., *Antisense N. A. Drug Dev.* 7:151 (1997).
Sullenger et al., *Cell.* 63:601-608 (1990).
Sun, *Curr. Opin. Mol. Ther.* 2:100 (2000).
Szostak, *TIBS* 17:89-93 (1993).
Tang et al., *RNA* 3:914 (1997).
Torrence et al., *Proc. Natl. Acad. Sci. USA* 90:1300 (1993).
Uhlenbeck, *Nature* 328:596 (1987).
Usman & McSwiggen, *Ann. Rep. Med. Chem.* 30:285-294 (1995).
Usman and Cedergren, *Trends in Biochem. Sci.* 17:334-339 (1992).
Usman et al., *J. Am. Chem. Soc.* 109:7845 (1987).
Vaish et al., *Biochem.* 36:6495 (1997).
Van Aerschot et al., *Nucl. And Nucl.* 7:75-90 (198874).
Van Ness et al., *Nucl. Acids Res.* 19:3345-3350 (1991).
Verma and Eckstein, *Annu. Rev. Biochem.* 67:99-134 (1998).
Warashina et al., *Chem. And Biol.* 6:237-250 (1999).
Weetall et al., *Methods in Enzymol.ogy* 34:59-72 (1974).
Werner and Uhlenbeck "The effect of base mismatches in the substrate recognition helices of hammerhead ribozymes on binding and catalysis," *Nucl. Acids Res.* 23:2092-2096 (1995).
Wincott et al., *Methods Mol. Biol.* 74:59 (1997).
Wincott et al., *Nucl. Acids Res.* 23:2677-2684 (1995).
Woo-Pong, *BioPharm* 20:33 (Nov. 1994).
Zaug, *Nature* 324:429 (1986).
Office Action mailed on Jun. 17, 2003 for U.S. Appl. No. 09/887,182, 11 pages.
Office Action mailed on Sep. 24, 2004 for U.S. Appl. No. 09/887,182, 10 pages.

* cited by examiner

Figure 1. Chemical synthesis of Oligonucleotides

Figure 2

| Chemical Structure | Alias | Product Yield | Efficiency |
|---|---|---|---|
| 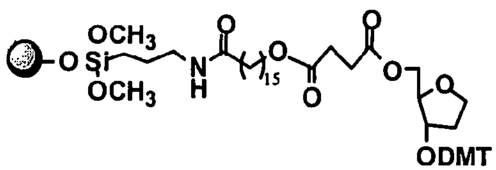 | 22 atom CPG, HDDA CPG | 230 - 240 ODs/umol | 80% |
| 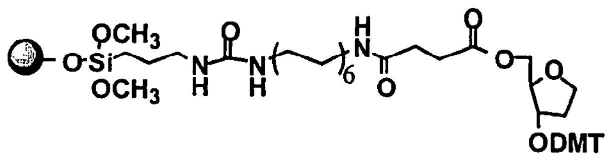 | 20 atom CPG, UDDA | 270 - 280 ODs/umol | 78-80% |
| 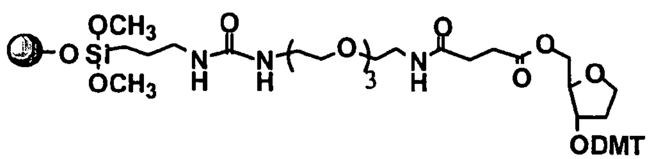 | 19 atom CPG, PEG CPG | 280 - 290 ODs/umol | 85-87% |

ODMT - dimethoxytrityl

● - represents controlled pore glass (CPG)

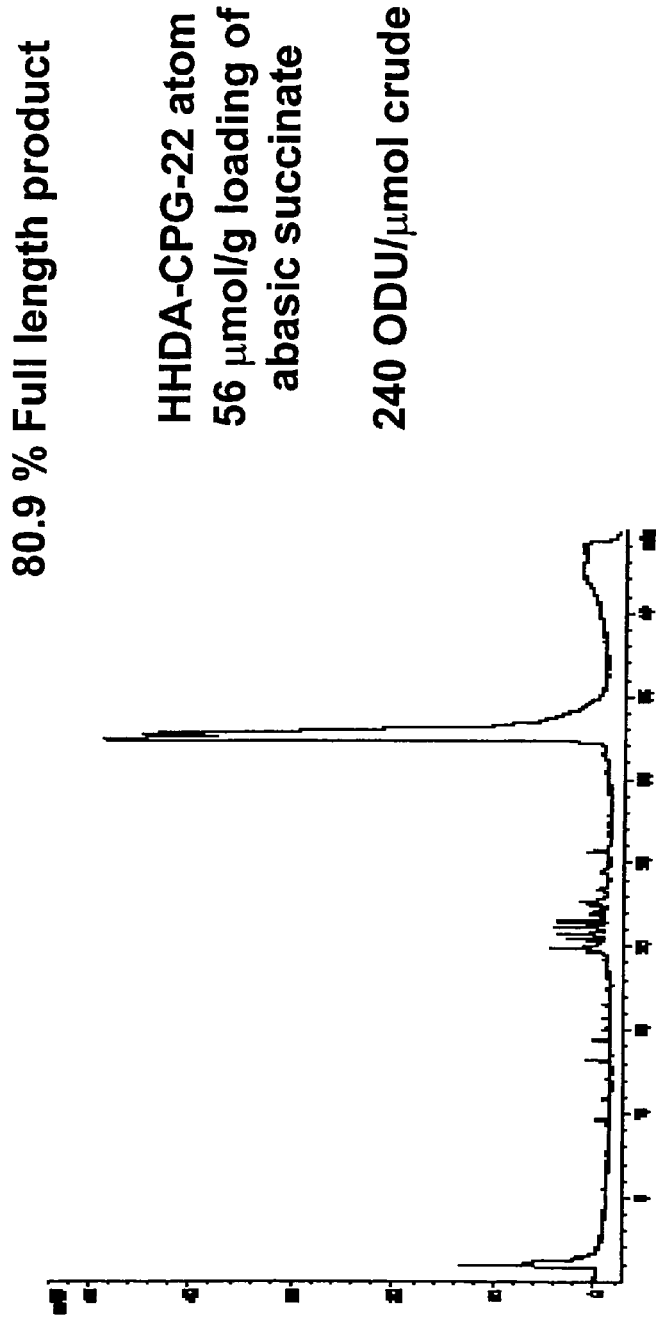
Figure 3. HPLC chromatograph of Ribozyme synthesized using CPG Linked HHDA Spacer
80.9 % Full length product
HHDA-CPG-22 atom
56 μmol/g loading of abasic succinate
240 ODU/μmol crude
Ribozyme Sequence: $g_s a_s g_s u_s$ ugcUGAuGaggccgaaaggccGaaAgucugB
Lower 2'-O-methyl modification
U-2'-C-allyl
S-phosphorothioate
B-3'-3' inverted abasic moiety
A,G-adenosine, guanosine

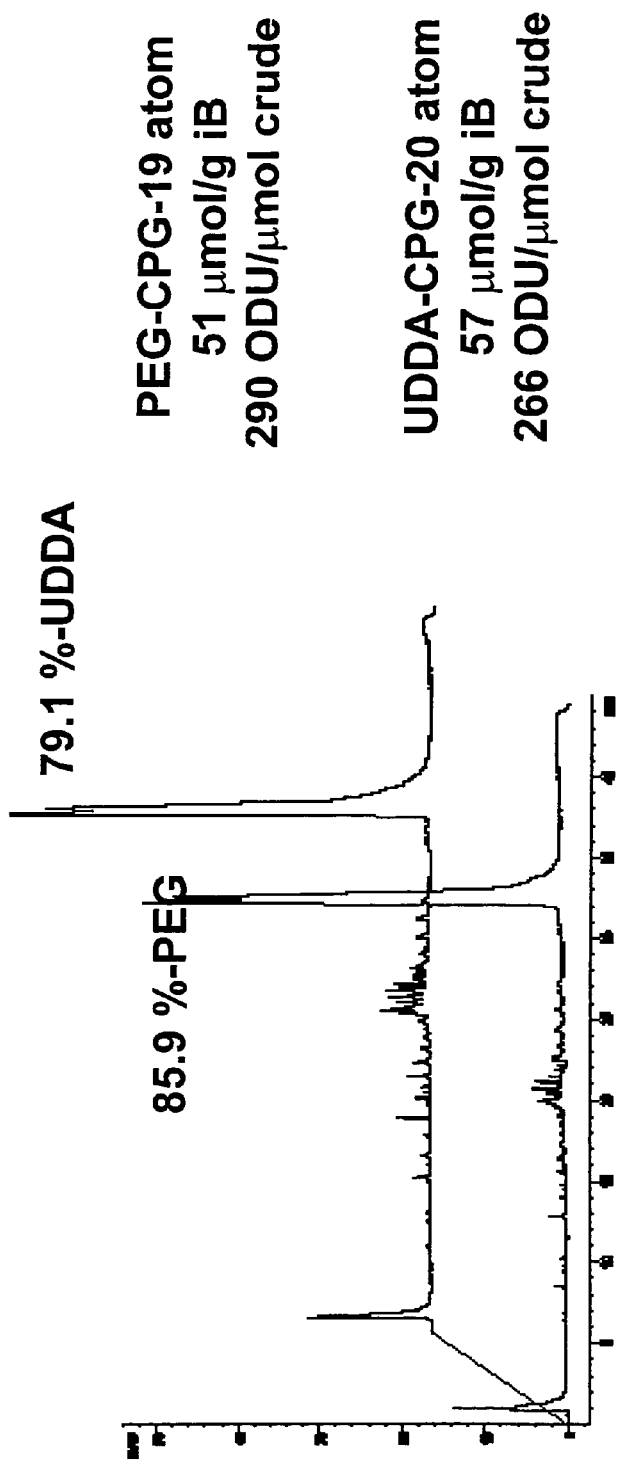
Figure 4. Synthesis of Ribozyme on CPG linked PEG and UDDA Spacers
Ribozyme Sequence: g$_s$a$_s$g$_s$u$_s$ugcUGAuGaggccgaaaggccGaaAgucugB
Lower 2'-O-methyl modification
U-2'-C-allyl
S-phosphorothioate
B-3'-3' inverted abasic moiety
A,G-adenosine, guanosine

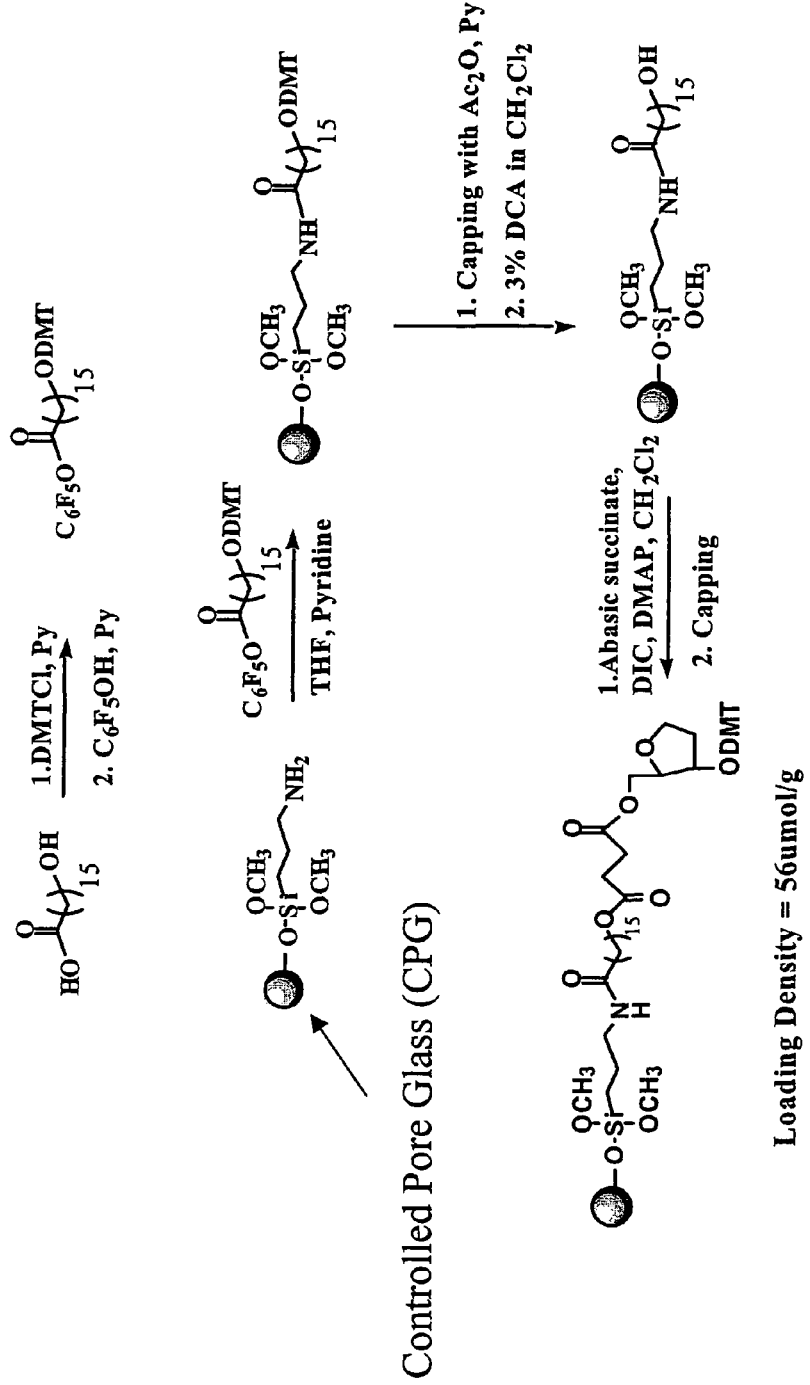
Figure 5. Synthesis of CPG linked HHDA CPG (22 atoms) Spacer

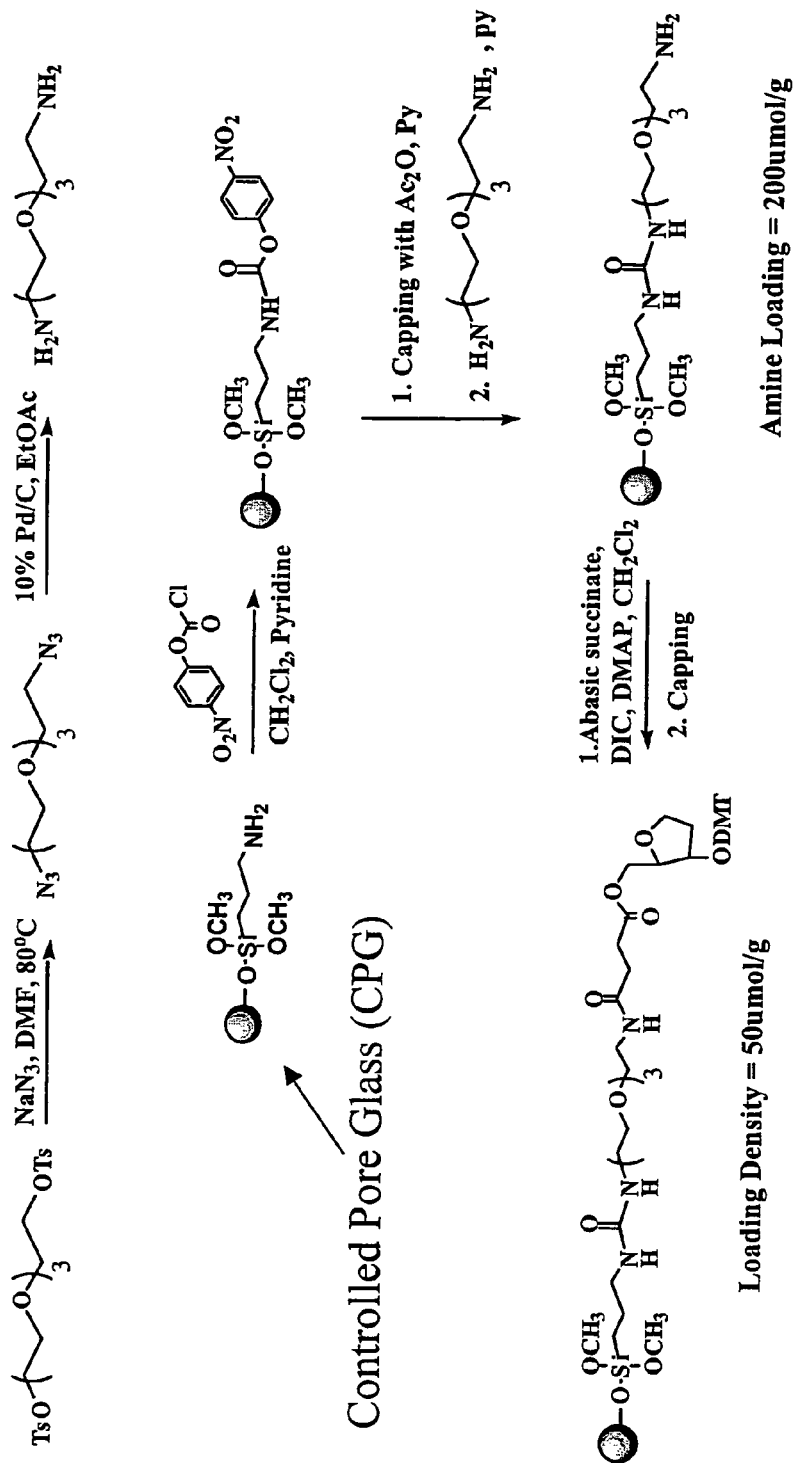
Figure 6. Synthesis of CPG-Linked PEG (19 atoms) Spacer

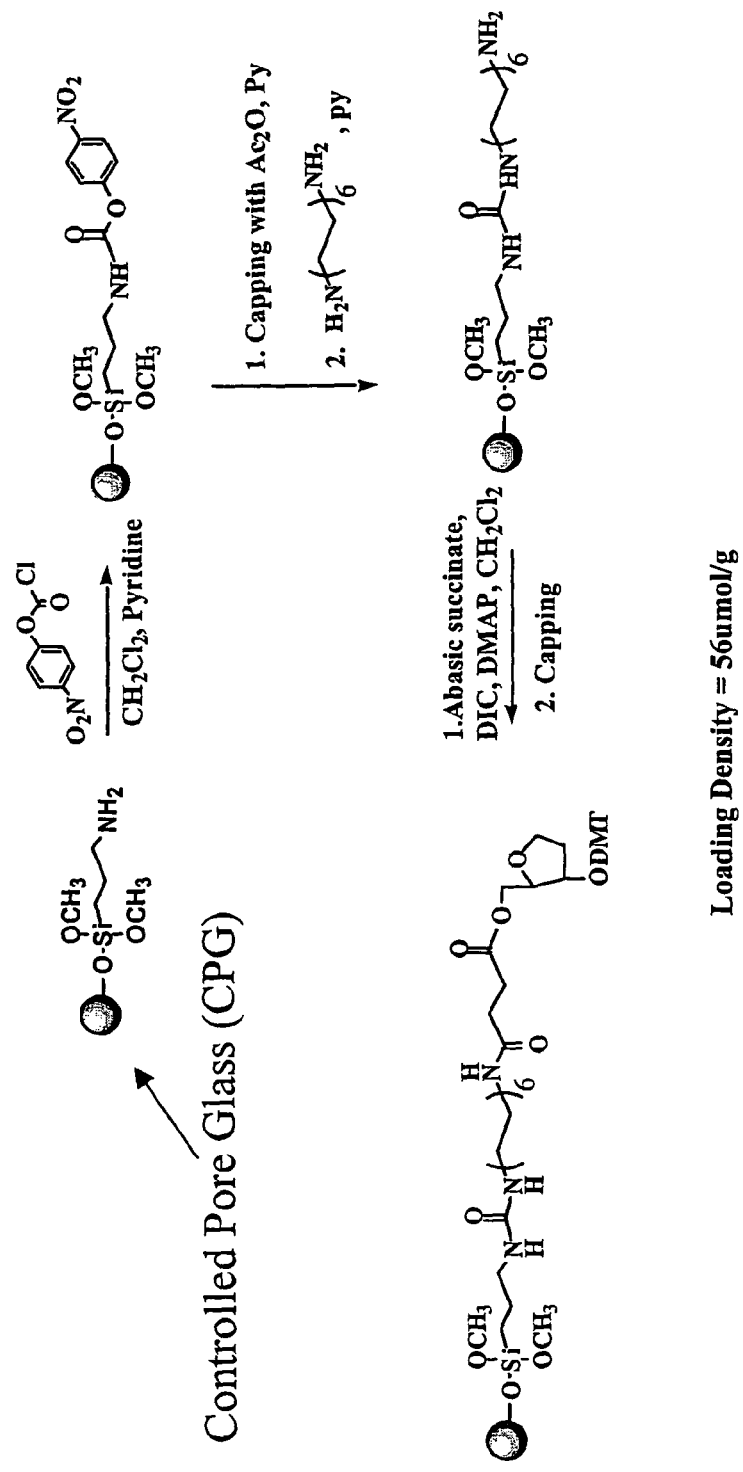
Figure 7. Synthesis of CPG linked UDDA Spacer

Figure 8. General Chemical formulae for Spacers
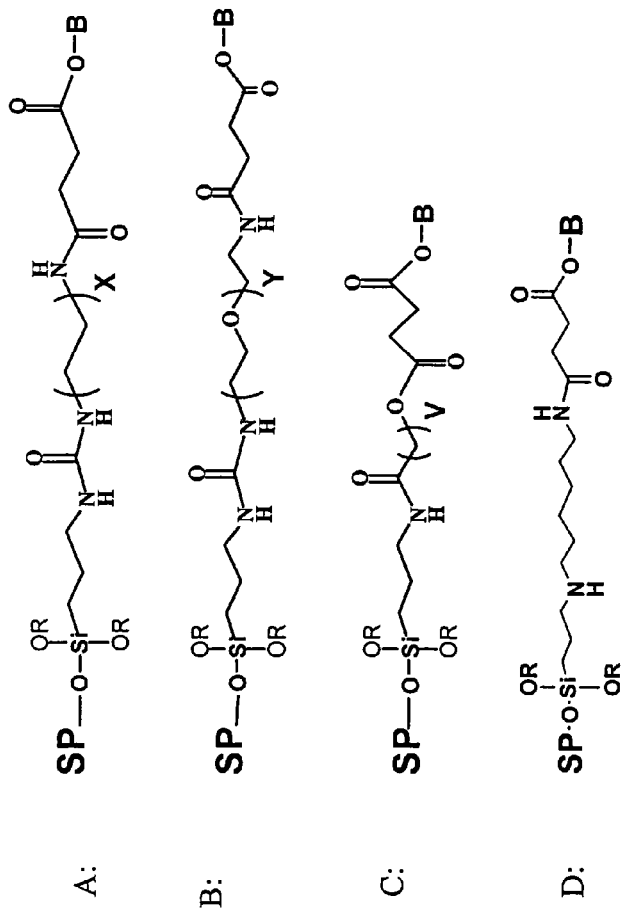
SP- solid support
B- terminal chemical group
X- integer between 2 and 6 (i.e. 2, 3, 4, 5, 6)
Y-integer between 1 and 4 (i.e. 1,2,3,4)
V-integer between 5 and 16 (i.e. 5,6,7,8,9,10,11,12,13,14,15,16)
R- represents a moiety selected from a group comprising alkyl, alkenyl, alkynyl, aryl, alkylaryl, carbocyclic aryl, heterocyclic aryl, and the like

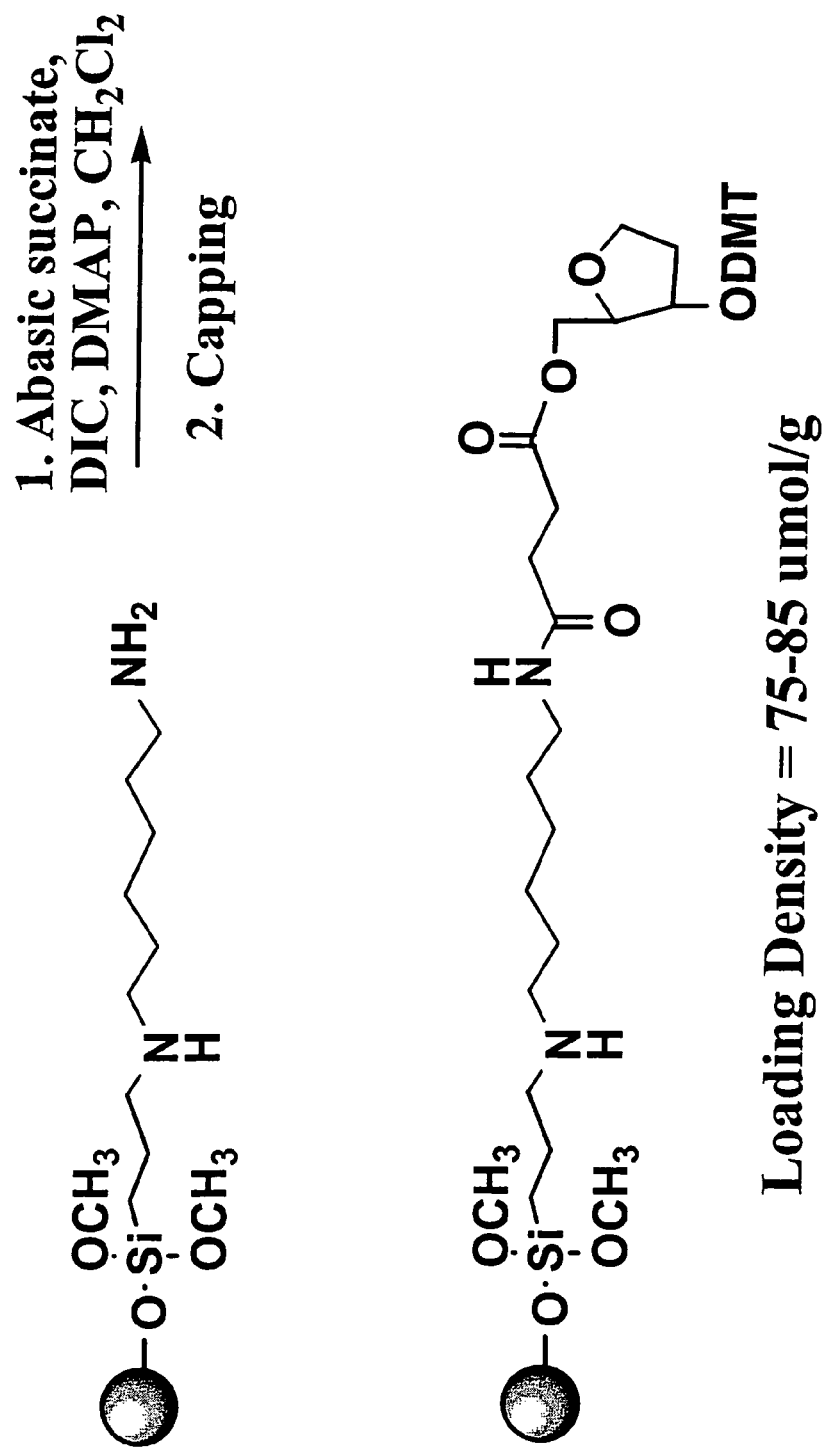

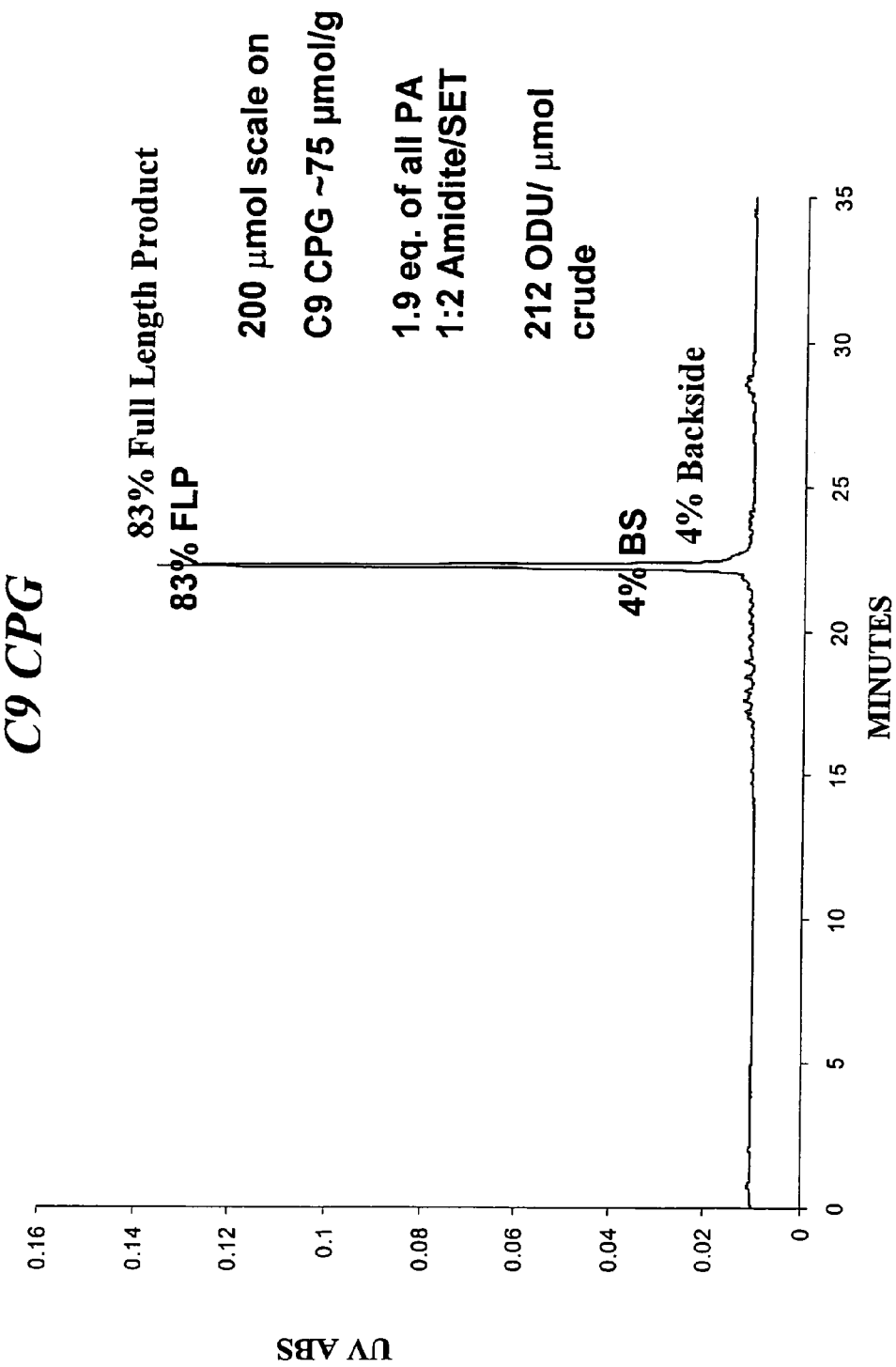

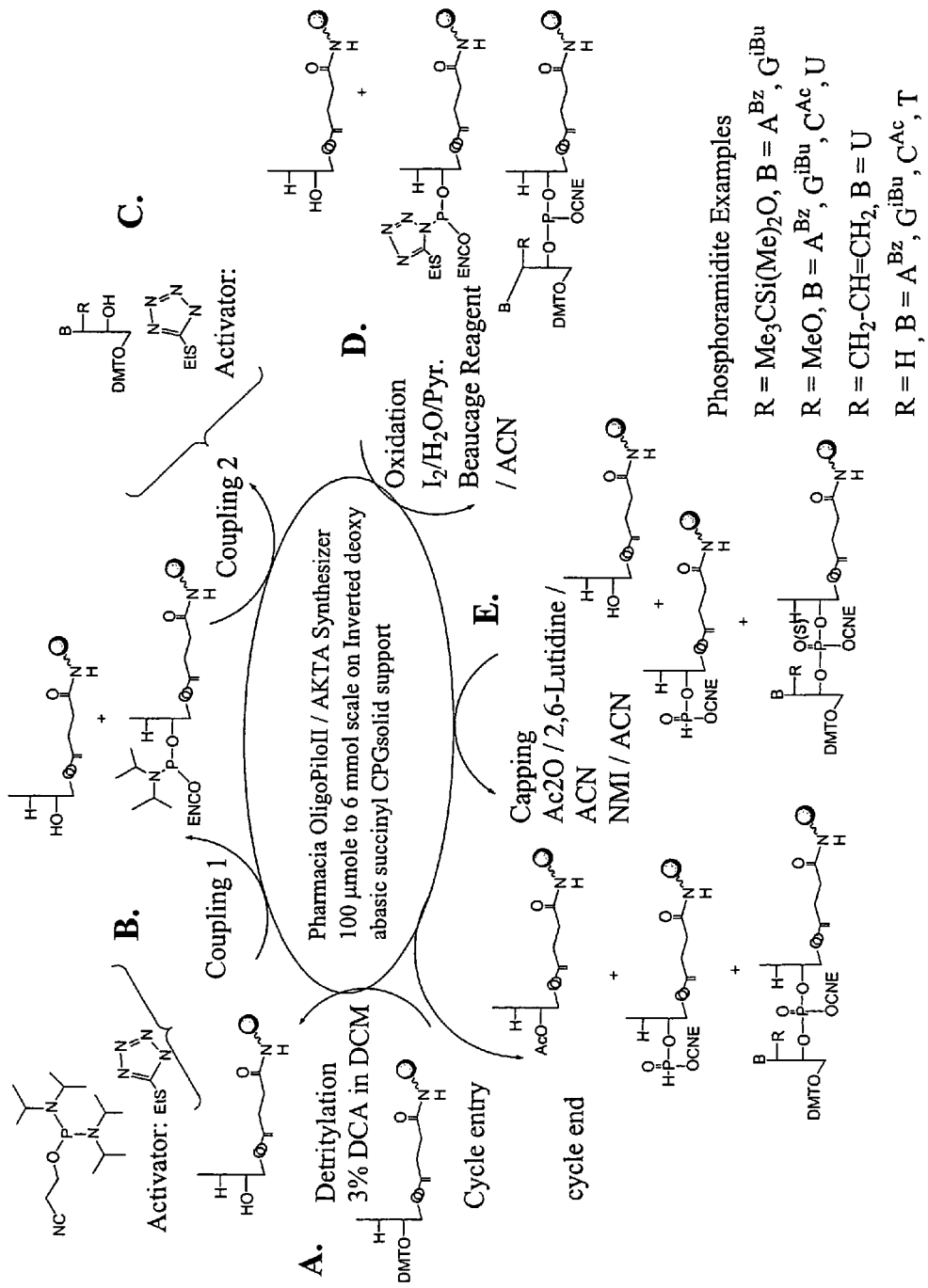
Figure 11: Chemical Synthesis of Oligonucleotides, in situ Phosphoramidite

SEQUENCE LISTING

```
<160> NUMBER OF SEQ ID NOS: 1

<210> SEQ ID NO 1
<211> LENGTH: 34
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: 2'-O-methyl
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: misc_feature
<222> LOCATION: (8)..(8)
<223> OTHER INFORMATION: 2'-C-allyl
<220> FEATURE:
<221> NAME/KEY: misc_feature
<222> LOCATION: (11)..(11)
<223> OTHER INFORMATION: 2'-O-methyl
```

```
<220> FEATURE:
<221> NAME/KEY: misc_feature
<222> LOCATION: (13)..(25)
<223> OTHER INFORMATION: 2'-O-methyl
<220> FEATURE:
<221> NAME/KEY: misc_feature
<222> LOCATION: (27)..(28)
<223> OTHER INFORMATION: 2'-O-methyl
<220> FEATURE:
<221> NAME/KEY: misc_feature
<222> LOCATION: (30)..(34)
<223> OTHER INFORMATION: 2'-O-methyl
<220> FEATURE:
<221> NAME/KEY: misc_feature
<222> LOCATION: (34)..(34)
<223> OTHER INFORMATION: inverted abasic moiety

<400> SEQUENCE: 1
gaguugcuga ugaggccgaa aggccgaaag ucug                              34
```

METHOD FOR THE CHEMICAL SYNTHESIS OF OLIGONUCLEOTIDES

This application is a divisional of Ser. No. 09/887,182 now U.S. Pat. No. 6,995,259, filed Jun. 22, 2001, which is a continuation-in-part of Vargeese et al. U.S. patent application Ser. No. 09/426,079, filed Oct. 22, 1999, now abandoned, which is a continuation in part of Vargeese et al., U.S. patent application Ser. No. 09/178,154, filed Oct. 23, 1998.

BACKGROUND OF THE INVENTION

SEQUENCE LISTING

The sequence listing submitted via EFS, in compliance with 37 CFR §1.52(e)(5), is incorporated herein by reference. The sequence listing text file submitted via EFS contains the file "SequenceListing67USDIV," created on Feb. 22, 2010, which is 1,058 bytes in size.

This invention relates to a novel method for the chemical synthesis of oligonucleotides, including RNA, DNA, chimeric oligonucleotides, and chemically modified nucleic acids. Specifically, the invention concerns novel processes for synthesis of oligonucleotides using controlled pore glass solid support.

The following is a discussion of relevant art, none of which is admitted to be prior art to the present invention.

Chemical synthesis of oligonucleotides can be accomplished using a number of protocols, including the use of solid support chemistry, where an oligonucleotide is synthesized one nucleoside at a time while anchored to an inorganic polymer. The first nucleotide is attached to an inorganic polymer using a reactive group on the polymer, which reacts with a reactive group on the nucleoside to form a covalent linkage. Each subsequent nucleoside is then added to the first nucleoside molecule by: 1) formation of a phosphite linkage between the original nucleoside and a new nucleoside with a protecting group; 2) conversion of the phosphite linkage to a phosphate linkage by oxidation; and 3) removal of one of the protecting groups to form a new reactive site for the next nucleoside (Caruthers & Matteucci, U.S. Pat. Nos. 4,458,066; 5,153,319; 5,132,418; 4,973,679 all of which are incorporated by reference herein). Solid phase synthesis of oligonucleotides eliminates the need to isolate and purify the intermediate products after the addition of every nucleotide base.

Following the synthesis of RNA, the oligonucleotides is deprotected (Wincott et al., supra) and purified to remove by-products, incomplete synthesis products, and the like.

The demand for oligonucleotides for use as therapeutic agents, diagnostics, and research reagents has created the need for the efficient cost effective large scale manufacture of these compounds. Currently, efforts have focused on improving the coupling efficiency and the maximization of yield in phosphoramidite based synthesis. However, another area that deserved attention in this approach is the overall time and cost of preparing the nucleoside phosphoramidite reagents to be used as raw materials in the manufacture of oligonucleotides. The use of in situ phosphoramidite generation in the synthesis of oligonucleotides is an attempt to overcome the limitations imposed on the synthesis and isolation of phosphoramidites. By generating reactive nucleoside intermediates during the actual synthesis of the oligonucleotide, the need for separate phosphoramidite manufacture is overcome. However, efforts thus far have relied upon the in situ generation of 5'-O-protected nucleoside 3'-O-phosphoramidites that are coupled with 5'-OH nucleophiles. This approach is problematic in that dimerization of the intended 5'-O-protected nucleoside 3'-O-phosphoramidites occurs as a competing reaction, thereby reducing the effective equivalents of phosphoramidite available for coupling.

Tracz, U.S. Pat. No. 5,686,599, describes a method for one pot deprotection of RNA under conditions suitable for the removal of the protecting group from the 2' hydroxyl position.

Usman et al., U.S. Pat. No. 5,804,683, describes a method for the removal of exocyclic protecting groups using alkylamines.

Wincott et al., U.S. Pat. No. 5,831,071, describes a method for the deprotection of RNA using ethylamine, propylamine, or butylamine.

Vinayak, U.S. Pat. No. 5,281,701, describes methods and reagents for the synthesis of RNA using 5'-O-protected-2'-O-alkylsilyl-adenosine phosphoramidite and 5'-O-protected-2'-O-alkylsilylguanosine phosphoramidite monomers which are deprotected using ethylthiotetrazole.

Usman and Cedergren, *Trends in Biochem. Sci.* 1992, 17, 334-339 describe the synthesis of RNA-DNA chimeras for use in studies of the role of 2' hydroxyl groups.

Sproat et al., 1995 *Nucleosides & Nucleotides* 14, 255-273, describe the use of 5-ethylthio-1H-tetrazole as an activator to enhance the quality of oligonucleotide synthesis and product yield.

Gait et al., 1991, *Oligonucleotides and Analogues*, ed. F. Eckstein, Oxford University Press 25-48, describe general methods for the synthesis of RNA.

Koester and Coull, U.S. Pat. No. 4,923,901; Klem and Riley, U.S. Pat. No. 5,723,599; Furukawa et al., U.S. Pat. No. 5,674,856; Nelson, U.S. Pat. No. 5,141,813; Reed et al., U.S. Pat. No. 5,419,966; Caruthers and Matteucci, U.S. Pat. No. 4,458,066; Bhatt, U.S. Pat. No. 5,252,723; Weetall et al., 1974 ,*Methods in Enzymology,* 34, 59-72; Van Aerschot et al., 1988, *Nucleosides and Nucleotides,* 7, 75-90; Maskos and Southern, 1992, *Nucleic Acids Research,* 20, 1679-1684; Van Ness et al., 1991, *Nucleic Acids Research,* 19, 3345-3350; Katzhendler et al., 1989, *Tetrahedron,* 45, 2777-2792; Hovinen et al., 1994, *Tetrahedron,* 50, 7203-7218; Nippon Shinyaku, GB 2,169,605; Boehringer Mannheim, EP 325,970; Reddy and Michael, International PCT publication No. WO 94/01446; Akad. Wiss. DDR, E. German patent No. 280,968; and Bayer, W. German patent No. 4,306,839, all describe specific examples of solid supports for oligonucleotide synthesis and specific methods of use for certain oligonucleotides.

Zhang and Tang, International PCT Publication No. WO 97/42202; and Kitamura et al., 2000, *Chem Lett.,* 10, 1134-1135 describe specific phosphitylating reagents and their use in oligonucleotide synthesis via in situ generation of 5'-O-protected nucleoside 3'-O-phosphoramidites.

SUMMARY OF THE INVENTION

The present invention features compounds and reagents useful in the synthesis of oligonucleotides.

The efficiency of oligonucleotide synthesis is influenced by a number of variables including the form of solid support utilized, the length and type of spacer, and the type of chemical bond utilized as a linker between the spacer and the first nucleoside (Katzhendler et al., 1989, *Tetrahedron* 45, 2777-2792). The effects of modifying the spacer length has been investigated to determine the optimal length for efficient synthesis of DNA oligonucleotides (Katzhendler et al., 1987, *Reactive Polymers* 6, 175-187; Katzhendler et al, 1989, *Tetrahedron* 45, 2777).

For example Katzhendler et al, 1989, supra, state that for the synthesis of DNA:

"[s]pacers made up of only 12-21 atoms in length, produced poor results relatives to end product purity, homogeneity and yield. Purer products were obtained on spacers with lengths of at least 24 atoms".

The authors further indicate that the efficiency of DNA synthesis will be relatively high so long as the spacer length is at least 24 atoms. They further suggest that the poor efficiency of DNA synthesis using 12-24 atom spacers is caused by a tendency of these spacers to bend towards the solid support. The bent spacer would allow for increased stabilization of the solid support due to inter-chain stabilization, but would negatively impact DNA oligonucleotide synthesis.

Applicant has surprisingly found that the use of specific spacers having lengths between about 9 to about 24 atoms can be utilized for the efficient synthesis of oligonucleotides. These spacers have been utilized by applicant to produce high yields of oligonucleotides with increased purity.

In one embodiment, the invention features derivatized solid support compositions useful in the synthesis of oligonucleotides and methods of use, wherein the derivatized solid support comprises a spacer molecule of about 9-24 atoms in length.

In another embodiment, the invention features a compound having Formula I:

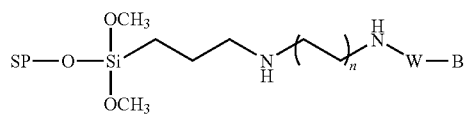

wherein SP represents a solid support comprising controlled pore glass; polystyrene; silica gel; cellulose paper; polyamide/kieselgur; or polacryloylmorpholide, n is an integer from about 1 to about 6, B represents a terminal chemical group, for example a nucleic acid, nucleoside, nucleotide, or non-nucleosidic derivative with or without protecting groups, and W represents a chemical linkage, for example a succinyl, oxalyl, hydroquinone-O—O'-diacetic acid, or photolabile linker. W and B together can comprise a terminal chemical group, for example a 5-O-succinyl-3-O-dimethoxytrityl nucleoside or abasic derivative.

In another embodiment, the invention features a compound having Formula II:

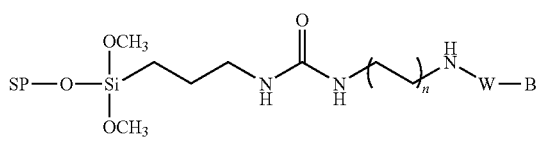

wherein SP represents a solid support, for example controlled pore glass; polystyrene; silica gel; cellulose paper; polyamide/kieselgur; or polacryloylmorpholide, n is an integer from about 1 to about 6, B represents a terminal chemical group, for example a nucleic acid, nucleoside, nucleotide, or non-nucleosidic derivative with or without protecting groups, and W represents a chemical linkage, for example a succinyl, oxalyl, hydroquinone-O—O'-diacetic acid, or photolabile linker. W and B together can comprise a terminal chemical group, for example a 5-O-succinyl-3-O-dimethoxytrityl nucleoside or abasic derivative.

In another embodiment, the invention features a compound having Formula III:

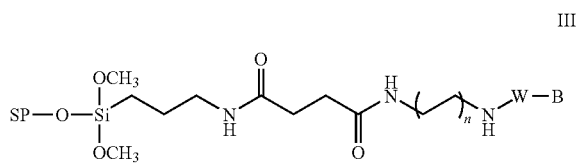

wherein SP represents a solid support, for example controlled pore glass; polystyrene; silica gel; cellulose paper; polyamide/kieselgur; or polacryloylmorpholide, n is an integer from about 1 to about 6, B represents a terminal chemical group, for example a nucleic acid, nucleoside, nucleotide, or non-nucleosidic derivative with or without protecting groups, and W represents a chemical linkage, for example a succinyl, oxalyl, hydroquinone-O—O'-diacetic acid, or photolabile linker. W and B together can comprise a terminal chemical group, for example a 5-O-succinyl-3-O-dimethoxytrityl nucleoside or abasic derivative.

In another embodiment, the invention features a compound having Formula IV:

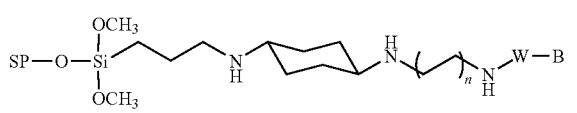

wherein SP represents a solid support, for example controlled pore glass; polystyrene; silica gel; cellulose paper; polyamide/kieselgur; or polacryloylmorpholide, n is an integer from about 1 to about 6, B represents a terminal chemical group, for example a nucleic acid, nucleoside, nucleotide, or non-nucleosidic derivative with or without protecting groups, and W represents a chemical linkage, for example a succinyl, oxalyl, hydroquinone-O—O'-diacetic acid, or photolabile linker. W and B together can comprise a terminal chemical group, for example a 5-O-succinyl-3-O-dimethoxytrityl nucleoside or abasic derivative.

In one embodiment, the invention features a compound having Formula V:

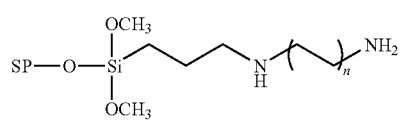

wherein SP represents a solid support, for example controlled pore glass; nylon, polystyrene; silica gel; cellulose paper; polyamide/kieselgur; or polacryloylmorpholide, and n is an integer from about 1 to about 6.

In another embodiment, the invention features a compound having Formula VI:

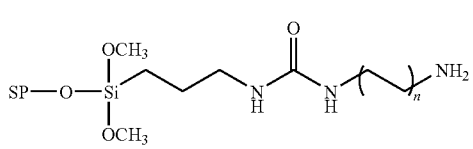

VI wherein SP represents a solid support, for example controlled pore glass; nylon, polystyrene; silica gel; cellulose paper; polyamide/kieselgur; or polacryloylmorpholide, and n is an integer from about 1 to about 6.

In another embodiment, the invention features a compound having Formula VII:

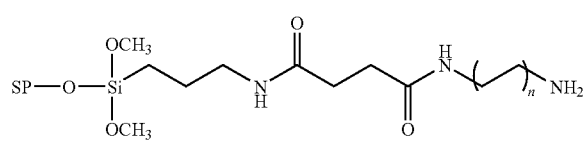

VII wherein SP represents a solid support, for example controlled pore glass; nylon, polystyrene; silica gel; cellulose paper; polyamide/kieselgur; or polacryloylmorpholide, and n is an integer from about 1 to about 6.

In another embodiment, the invention features a compound having Formula VIII:

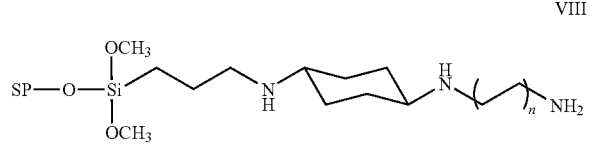

VIII wherein SP represents a solid support, for example controlled pore glass; nylon, polystyrene; silica gel; cellulose paper; polyamide/kieselgur; or polacryloylmorpholide, and n is an integer from about 1 to about 6.

In another embodiment the invention features a method ("method A") for solid phase synthesis of oligonucleotides comprising: 5'-deblocking, coupling, oxidation, and capping, wherein these steps are repeated under conditions suitable for the synthesis of an oligonucleotide, and wherein the synthesis of the oligonucleotide is initiated on a derivatized solid support linked to a terminal chemical group via a spacer molecule, wherein the derivatized solid support linked to the terminal chemical group comprises a structure having Formula I, II, III or IV.

In another embodiment the invention features a method ("method B") for solid phase synthesis of oligonucleotides comprising: 5'-deblocking, coupling, oxidation, and capping, wherein these steps are repeated under conditions suitable for the synthesis of an oligonucleotide, and wherein the synthesis of the oligonucleotide is initiated on a derivatized solid support linked to a terminal chemical group via a spacer molecule, wherein the derivatized solid support linked to the terminal chemical group comprises a structure having Formula IX:

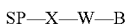

IX wherein, SP represents a solid support, for example controlled pore glass; nylon, polystyrene; silica gel; cellulose paper; polyamide/kieselgur; or polacryloylmorpholide; X represents a spacer comprising a linear chemical moiety Y-Z-W comprised of carbon, silicon, hydrogen, nitrogen, sulfur, and/or oxygen atoms where Z is a diradical chemical moiety of between 10 and 24 atoms, preferably 10, 11, 12, 13, 14, 15, 16, 17, 18, 19, 20, 21, 22, 23, or 24 atoms, Y and W independently comprise a chemical linkage, wherein the chemical linkage Y between SP and X comprises a silyl ether, urea, amide, or carbamate linkage and the chemical linkage W between the X and B comprises a carboxy, amino, carboxamido, mercaptoalkyl, succinyl, oxalyl, or photolabile linker (e.g. 3'glycolate termini, o-nitrophenyl-1,3-propanediol), acid labile linker (e.g. alkoxybenzylidene acetal, hydroquinone-O,O'-diacetic acid), or pentachlorophenylsuccinate, (Pon et al., 1988, *Biotechniques* 6, 768-775; Palom et al., 1993, *Tetrahedron Lett.* 34, 2195-2198; Greenberg, 1995, *Tetrahedron* 51, 29-38; Hovinen et al., 1994, *Tetrahedron* 50, 7203-7213; Palom et al., 1991, *Tetrahedron Lett* 34, 2195-2198; Pon & Yu, 1997, *Tetrahedron Lett* 38, 3327-3330; Dell-Aquila et al., 1997, *Tetrahedron Lett.* 38, 5289-5292; Birch-Hirschfeld et al., 1994, *Nucleic Acids Research* 22, 1760-1761; Alul et al., 1991, *Nucleic Acids Research* 19, 1527-1532, all of which are incorporated by reference herein in their entirety); B represents a terminal chemical group, such as, for example, a nucleic acid, nucleoside, nucleotide, or non-nucleosidic derivative with or without protecting groups. W and B together can comprise a terminal chemical group, for example a 5-O-succinyl-3-O-dimethoxytrityl nucleoside or abasic derivative, where B can be linked to the oligonucleotide being synthesized via 3'-5', 3'-2', or 3'-3' linkages. Non-limiting examples of general formulae for spacers of the present invention are given in FIG. 8.

In another embodiment the invention features a method ("method C") for solid phase synthesis of oligonucleotides comprising: 5'-deblocking, 5'-activation, coupling, oxidation, and capping, wherein these steps are repeated under conditions suitable for the synthesis of an oligonucleotide, and wherein 5'-activation comprises the in situ formation of an activated 5'-phosphorus species and coupling comprises the nucleophilic attack of the activated 5'-phosphorus species under conditions suitable for covalent attachment of the nucleophile to the activated 5'-phosphorus species, and wherein the synthesis of the oligonucleotide is initiated on a derivatized solid support linked to a terminal chemical group via a spacer molecule, wherein the derivatized solid support linked to the terminal chemical group comprises a structure having Formula I, II, III or IV.

In another embodiment the invention features a method ("method D") for solid phase synthesis of oligonucleotides comprising: 5'-deblocking, 5'-activation, coupling, oxidation, and capping, wherein these steps are repeated under conditions suitable for the synthesis of an oligonucleotide, and wherein 5'-activation comprises the in situ formation of an activated 5'-phosphorus species and coupling comprises the nucleophilic attack of the activated 5'-phosphorus species under conditions suitable for covalent attachment of the nucleophile to the activated 5'-phosphorus species, and wherein the synthesis of the oligonucleotide is initiated on a derivatized solid support linked to a terminal chemical group via a spacer molecule, wherein the derivatized solid support linked to the terminal chemical group comprises a structure having Formula IX:

SP—X—W—B                IX wherein, SP represents a solid support, for example controlled pore glass; nylon, polystyrene; silica gel; cellulose paper; polyamide/kieselgur; or polacryloylmorpholide; X represents a spacer comprising a linear chemical moiety Y-Z-W comprised of carbon, silicon, hydrogen, nitrogen, sulfur, and/or oxygen atoms where Z is a di-radical chemical moiety of between 10 and 24 atoms, preferably 10, 11, 12, 13, 14, 15, 16, 17, 18, 19, 20, 21, 22, 23, or 24 atoms, Y and W independently comprise a chemical linkage, wherein the chemical linkage Y between SP and X comprises a silyl ether, urea, amide, or carbamate linkage and the chemical linkage W between the X and B comprises a carboxy, amino, carboxamido, mercaptoalkyl, succinyl, oxalyl, or photolabile linker (e.g. 3'glycolate termini, o-nitrophenyl-1,3-propanediol), acid labile linker (e.g. alkoxybenzylidene acetal, hydroquinone-O,O'-diacetic acid), or pentachlorophenyl-succinate, (Pon et al., 1988, *Biotechniques* 6, 768-775; Palom et al., 1993, *Tetrahedron Lett.* 34, 2195-2198; Greenberg, 1995, *Tetrahedron* 51, 29-38; Hovinen et al., 1994, *Tetrahedron* 50, 7203-7213; Palom et al., 1991, *Tetrahedron Lett* 34, 2195-2198; Pon & Yu, 1997, *Tetrahedron Lett* 38, 3327-3330; Dell-Aquila et al., 1997, *Tetrahedron Lett.* 38, 5289-5292; Birch-Hirschfeld et al., 1994, *Nucleic Acids Research* 22, 1760-1761; Alul et al., 1991, *Nucleic Acids Research* 19, 1527-1532, all of which are incorporated by reference herein in their entirety); B represents a terminal chemical group, for example a nucleic acid, nucleoside, nucleotide, or non-nucleosidic derivative with or without protecting groups. W and B together can comprise a terminal chemical group, for example a 5-O-succinyl-3-O-dimethoxytrityl nucleoside or abasic derivative, where B can be linked to the oligonucleotide being synthesized via 3'-5', 3'-2', or 3'-3' linkages; Non-limiting examples of general formulae for spacers of the present invention are given in FIG. 8.

In one embodiment, "B" of Formulae I, II, III, IV and IX comprises a nucleic acid, nucleoside, nucleotide, or non-nucleosidic derivative comprising an acid labile protecting group, for example a dimethoxytrityl, monomethoxytrityl, or other trityl group.

In another embodiment, the chemical linkage "W" between "B" of Formulae I, II, III, IV and IX and the spacer molecule "X" comprises a succinyl linker.

In another embodiment, "X" in Formula IX comprises Formula X:

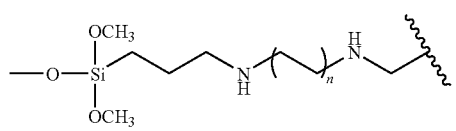

wherein n is an integer from about 1 to about 6.

In another embodiment, "X" in Formula IX comprises Formula XI:

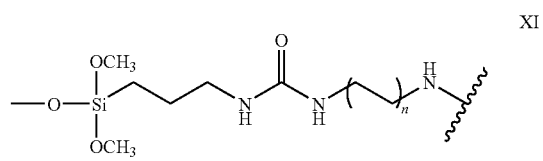

wherein n is an integer from about 1 to about 6.

In another embodiment, "X" in Formula IX comprises Formula XII:

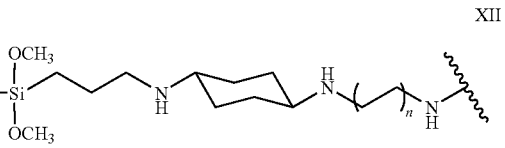

wherein n is an integer from about 1 to about 6.

In one embodiment, the invention features a method of synthesizing a compound having Formula V, where n=3, comprising silanization of native Controlled Pore Glass (CPG) with N-(6-aminohexyl)aminopropyl trimethoxy silane under conditions suitable for the formation of a compound having Formula V.

In another embodiment, the coupling of the terminal chemical group B to the compound of Formula V results in a compound of Formula I. In yet another embodiment, the coupling of the terminal chemical group B to the compound of Formula V is at a loading from about 50 to about 100 umol/gram of CPG, or about 75 to about 85 umol/gram of CPG.

In another embodiment, the coupling of the terminal chemical group B to the compound of Formula VI results in a compound of Formula II. In yet another embodiment, the coupling of the terminal chemical group B to the compound of Formula VI is at a loading from about 40 to about 80 umol/gram of CPG, or about 50 to about 60 umol/gram of CPG.

In another embodiment, the coupling of the terminal chemical group B to the compound of Formula VII results in a compound of Formula III. In yet another embodiment, the coupling of the terminal chemical group B to the compound of Formula VII is at a loading from about 40 to about 80 umol/gram of CPG, or about 50 to about 60 umol/gram of CPG.

In another embodiment, the coupling of the terminal chemical group B to the compound of Formula VIII results in a compound of Formula IV. In yet another embodiment, the coupling of the terminal chemical group B to the compound of Formula VIII is at a loading from about 40 to about 80 umol/gram of CPG, or about 50 to about 60 umol/gram of CPG.

In one embodiment, the invention features a method (Method E) for the synthesis of oligonucleotides comprising: 5'-deblocking, 5'-activation, coupling, oxidation, and capping, wherein these steps are repeated under conditions suitable for the synthesis of an oligonucleotide, and wherein 5'-activation comprises the in situ formation of an activated 5'-phosphorus species and coupling comprises the nucleophilic attack of the activated 5'-phosphorus species under conditions suitable for covalent attachment of the nucleophile to the activated 5'-phosphorus species.

In another embodiment, the 5'-activation contemplated by the invention comprises the in situ formation of a nucleoside 5'-O-phosphoramidite. In yet another embodiment, the nucleoside 5'-O-phosphoramidite of the invention is 5'-O-nucleoside 2-cyanoethyl-N,N-diisopropylphosphoramidite.

In another embodiment, the 5'-activation contemplated by the invention comprises the in situ formation of a nucleoside 5'-O-H-phosphonate, 5'-O-phosphotriester, 5'-O-pyrophosphate, or 5'-O-phosphate, wherein the oxidation step is either optional or omitted altogether.

In one embodiment, the 5'-activation contemplated by the invention comprises conjugation of a nucleoside 5'-hydroxyl with a phosphine in the presence of an activator. In another embodiment, the phosphine contemplated by the invention comprises cyanoethyl-(bis)-N,N-diisopropylphosphoramidite (2-cyanoethyl tetraisopropylphosphorodiamidite) and the activator comprises S-ethyl tetrazole (SET), tetrazole, or dicyanoimidazole (DCI).

In another embodiment, the 5'-activation contemplated by the invention comprises conjugation of a nucleoside 5'-hydroxyl with a phosphate in the presence of an activator. In another embodiment, the phosphate contemplated by the invention comprises a 2-chlorophenyl phosphorodichloridate or 2,5-dichlorophenyl phosphorodichloridate and the activator comprises 1-(mesitylsulfonyl)-3-nitro-1,2,4-1H-triazole (MSNT).

In another embodiment, the method for the synthesis of oligonucleotides comprising: 5'-deblocking, 5'-activation, coupling, oxidation, and capping is a solid phase synthesis, solution phase synthesis, or mixed phase synthesis.

In yet another embodiment, solid phase synthesis via Methods A-E of the invention is carried out on a solid support comprising silicon-based chips, controlled pore glass; polystyrene; nylon, silica gel; cellulose paper; polyamide/kieselgur; or polacryloylmorpholide.

In one embodiment, the conditions suitable for covalent attachment of the nucleophile to the activated 5'-phosphorus species in Method E of the invention comprises the use of an activator, or example S-ethyl tetrazole (SET), tetrazole, or dicyanoimidazole (DCI), in the presence of a 5'-protected or 5'-protected N-protected nucleoside bearing a nucleophile such as a hydroxyl group.

In one embodiment, Methods A-E of the invention are carried out on a reaction scale of about 0.1 umol to about 100 umol.

In another embodiment, Methods A-E of the invention are carried out on a reaction scale of about 100 umol to about 1 mmol.

In yet another embodiment, Methods A-E of the invention are carried out on a reaction scale of about 1 mmol to about 1 mol.

In yet another embodiment, Methods A-E of the invention are carried out on a reaction scale of about 1 mol to about 1000 mol.

In another, Methods A-E of the invention are carried out on a reaction scale of 3 to 300 mmol.

In one embodiment, Methods A-E of the invention is carried out on a oligonucleotide synthesizer, such as a flow through reactor or batch reactor synthesis platform, for example a Pharmacia OligoPilot, OligoProcess, Oligo-Max or AKTA synthesizer, Millipore 8800, or ABI 390Z platform.

In another embodiment, Methods A and B of the invention utilize between about 1.1 to about 2.0 equivalents of nucleoside phoshoramidite per coupling.

In yet another embodiment, Methods A and B of the invention utilize between about 2 to about 10 equivalents of activator per coupling.

In one embodiment, Methods C, D and E of the invention utilize between about 1.1 to about 10 equivalents of phosphine per coupling.

In yet another embodiment, Methods C, D and E of the invention utilize between about 1.1 to about 20 equivalents of activator per activation.

In another embodiment, the 5'-deblocking and 5'-activation steps contemplated by the invention can be applied to other positions within a nucleoside or non-nucleoside compound, for example when an inverted nucleoside or abasic derivative is included in the oligonucleotide. In such cases, 5'-deblocking and/or 5'-activation refers to the deblocking and activation of the corresponding group, such as a hydroxyl, that is intended to be substituted.

In one embodiment, "n" in Formula I of the invention is 3, "n" in Formula II of the invention is 6, "n" in Formula III of the invention is 3 or 6, or "n" in Formula IV of the invention is 3 or 6.

The number of atoms referred to in the spacer molecules contemplated by the invention, for example the Z component of "X" in Formula IX, refers to the number of linear atoms comprising the di-radical moiety that connects the solid support to the terminal chemical group, excluding the number of atoms in the chemical linker "W". For example, the Z component of "X" in Formula IX can comprise between 10 and 24 atoms. In another non-limiting example, a compound of Formula I, where n=3, is referred to as a 13 atom spacer molecule, since the spacer component of the molecule has nine carbon atoms, such a molecule can be referred to, for example, as a 13 atom C9 molecule.

The term "succinyl", "succinate" or "succinyl" linker as used herein refers to a structure as is known in the art comprising Formula XIII:

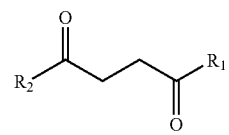

XIII including any salts thereof, for example triethylamine salts, wherein the succinate can comprise, for example a dimethoxytrityl (DMT) protected nucleoside ($R_1$) succinate such as 5'-O-DMT-3'-O-succinyl uridine, cytidine, thymidine, adenosine or guanosine or a non-nucleosidic ($R_1$) succinate such as a 5'-O-succinyl-3-O-dimethoxytrity deoxyribose derivative, where $R_2$ is H or a linker molecule attached to a solid support.

The structure:

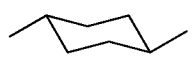

as used herein refers to a cyclohexane ring comprising para substitution in a cis or trans configuration.

The structure:

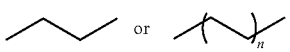

as used herein refers to a linear alkyl di-radical, wherein the length of the alkyl chain is specified by the number of carbons atoms shown, for example by the actual number of carbon atoms in the molecule or by the number of carbon atoms as determined by the integer value of "n". Compounds of the invention can include both saturated and unsaturated hydrocarbon chains in their structure, however, the exemplary structures shown comprise saturated hydrocarbon chains.

The term "protected" as used herein refers to a chemical moiety that is temporarily attached to a reactive chemical group to prevent the synthesis of undesired products during early stages of synthesis. The protecting group can then be removed to allow for the desired synthesis to proceed. Non-limiting examples of protecting groups are trityl, silyl, and acetyl groups.

The term "5'-deblocking" as used herein refers to a step in the synthesis of an oligonucleotide wherein a protecting group is removed from the terminal chemical group or previously added nucleoside, to produce a reactive hydroxyl, capable of contacting and reacting with a nucleoside molecule, for example a nucleoside phosphoramidite. One example of a protecting group that is removed is a trityl group, such as a dimethoxytrityl group.

The term "5'-activation" as used herein refers to a step in the synthesis of an oligonucleotide wherein an activated 5'-phosphorus species is generated in situ, for example when a nucleoside 5'-hydroxyl is conjugated with a phosphine or phosphate in the presence of an activator.

The term "coupling" as used herein refers to a step in the synthesis of an oligonucleotide wherein a nucleoside is covalently attached to the solid support or the terminal nucleoside residue of the oligonucleotide, for example via nucleophilic attack of an activated nucleoside phosphoramidite, H-phosphonate, phosphotriester, pyrophosphate, or phosphate in solution by a terminal 5'-hydroxyl group of the support bound nucleotide or oligonucleotide. The nucleoside phosphoramidite can be activated by using an activator reagent such as but not limited to, tetrazole, S-ethyl tetrazole, and/or 4,5-dicyanoimidazole (DCI).

The term "oxidation" as used herein refers to a step in the synthesis of an oligonucleotide wherein the newly synthesized phosphite bond is converted into phosphate bond. If the desired internucleotide linkage is phosphorothioate, the term "oxidation" also refers to the addition of a sulfur atom for the synthesis of a phosphorothioate linkage.

The term "capping" as used herein refers to a step in the synthesis of an oligonucleotide wherein a chemical moiety is covalently attached to any free or unreacted hydroxyl groups on the support bound spacer, nucleic acid or oligonucleotide. The capping step is used to prevent the formation of undesired products, for example sequences of shorter length than the desired sequence resulting from subsequent coupling reactions. In a non-limiting example, acetic anhydride can be utilized to cap the spacer, nucleic acid, or oligonucleotide with an acetyl group. This step can also be preformed prior to the oxidation of the phosphite bond rather than after oxidation.

The term "activator" as used herein refers to a compound that is used to generate a reactive phosphorus species, typically by displacing a less reactive group on a trivalent phosphorus atom. Example of activators include but are not limited to tetrazole, S-ethyl tetrazole (SET), dicyanoimidazole (DCI), or 1-(mesitylsulfonyl)-3-nitro-1,2,4-1H-triazole (MSNT).

The term "5'-activated phosphorus species" as used herein refers to a reactive phosphorus containing compound or phosphine, for example a nucleotide 5'-O-phosphoramidite, H-phosphonate, phosphotriester, pyrophosphate, triphosphate, or phosphate that is further activated via displacement of a chemical group from the phosphorus atom with a more reactive chemical group.

The term "phosphine" or "phosphite" as used herein refers to a trivalent phosphorus species, for example compounds having Formula XIV:

XIV wherein R can include the groups:

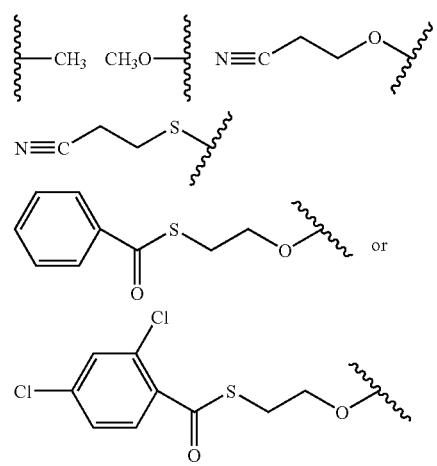

and wherein S and T independently include the groups:

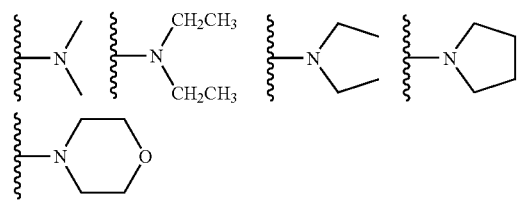

The term "pyrophosphate" as used herein refers to a cyclic phosphate species comprising three phosphorus atoms.

The term "triphosphate" as used herein refers to a linear phosphate species comprising three phosphorus atoms. Nucleoside triphosphate can be coupled via enzymatic activity, for example polymerase activity.

The term "H-phosphonate" as used herein refers to a pentavalent phosphorus with at least one hydrogen substituent.

The term "phosphate" as used herein refers to a pentavalent phosphorus species, for example a compound having Formula XV:

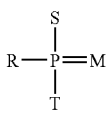

XV wherein R includes the groups:

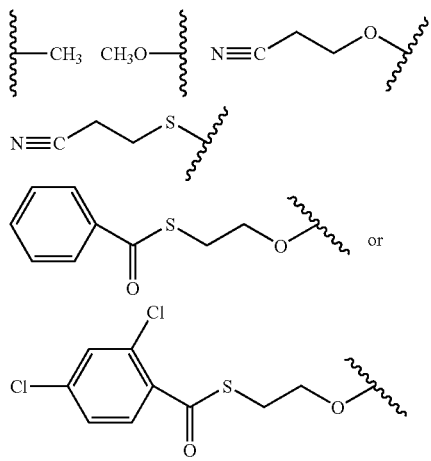

and wherein S and T each independently can be a sulfur or oxygen atom or a group which can include:

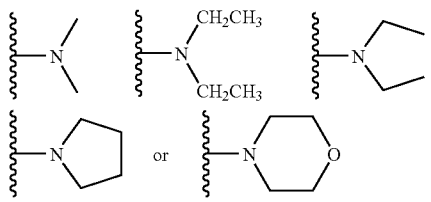

and wherein M comprises a sulfur or oxygen atom. The phosphate of the invention can comprise a nucleotide phosphate, wherein any R, S, or T in Formula XV comprises a linkage to a nucleic acid or nucleoside.

The term "phosphotriester" as used herein, refers to a trivalent phosphorus bearing three bonds to oxygen atoms The term "in situ" as used herein refers to the generation of a particular compound or reactive intermediate, for example a phosphoramidite of the invention, without purification and/or isolation.

The term "spacer" or "X" of Formula IX as used herein refers to a linear di-radical chemical moiety that links the solid support with the terminal chemical group "B" via another di-radical chemical moiety "W". The spacer maintains a degree of distance between the solid support and the oligonucleotide being synthesized. The spacer characteristics, such as length and chemical composition, can play an important role in the efficiency of RNA synthesis. The spacer is of sufficient length to allow the necessary reagents to access the oligoribonucleotide being synthesized. The spacer, is generally linked to a terminal chemical group such as a dimethoxytrityl protected nucleic acid or abasic derivative via a chemical linkage "W", for example a succinate linkage prior to the initiation of oligonucleotide synthesis. This linkage can be performed as a separate step resulting in the isolation of compounds of Formulae I, II, III, IV and IX, or can be formed as the first step in the synthesis of an oligonucleotide, for example, via derivatization of the solid support directly on an oligonucleotide synthesizer.

The term "solid support" as used herein refers to the material that is used as a scaffold from which oligonucleotide synthesis is initiated. A number of different solid supports suitable for the synthesis of oligonucleotides and methods for preparation are given by Pon, 1993, *Methods in Molecular Biology*, vol. 20: *Protocols for Oligonucleotides and Analogs*, Humana Press, which is incorporated herein by reference in its entirety.

The term "terminal chemical group" as used herein refers to a chemical entity attached via a spacer molecule or linker to a solid support from which an oligonucleotide can be synthesized. The terminal chemical group can comprise a terminal residue of the oligonucleotide being synthesized after the oligonucleotide is released from the solid support, for example a nucleoside, nucleotide, abasic derivative, or other chemical moiety that can be present at the 5' or 3' terminus of an oligonucleotide. In this example, the terminal chemical group can comprise a dimethoxytrityl (DMT) protected nucleoside succinate such as 5'-O-DMT-3'-O-succinyl uridine, cytidine, thymidine, adenosine or guanosine with without nitrogen protecting groups or a non-nucleosidic succinate such as a 5'-O-succinyl-3-O-dimethoxytrity deoxyribose derivative, where the succinyl portion of the terminal group is not present in the oligonucleotide after cleavage from the solid support. An oxylate derivative can be used in place of succinate derivatives contemplated by the invention. Alternately, the terminal chemical group can comprise a structure that is not present in the oligonucleotide after the oligonucleotide is released from the solid support, such as hydroquinone-O—O'-diacetic acid. A terminal chemical group derivatized to a solid support via a spacer or linker molecule that is not present in the oligonucleotide after the oligonucleotide is released from the solid support can be used as a universal scaffold for oligonucleotide synthesis since the composition of the oligonucleotide does not depend on the composition of the terminal chemical group, see for example Pon et al., 1999, *Nucleic Acids Research*, 27, 1531-1538).

The term "silanization" as used herein refers to the process of introducing a silyl, or silicon containing, group, for example to native glass. Silyl groups include, but are not limited to silyl ethers, alkylated silyl derivatives, or other substituted silyl groups.

The term "5'-hydroxyl protecting group compatible with oligonucleotide synthesis" or "acid labile protecting moiety" refers to a protecting group, such as the dimethoxytrityl, monomethoxytrityl, and/or trityl groups or other protecting groups, that can be used in a solid phase or solution phase oligonucleotide synthesis.

The term "phosphoramidite" as used herein refers to a nitrogen containing trivalent phosphorus derivative, for example, a 2-cyanoethyl-N,N-diisopropylphosphoramidite.

The term "alkyl" as used herein refers to a saturated aliphatic hydrocarbon, including straight-chain, branched-chain "isoalkyl", and cyclic alkyl groups. The term "alkyl" also comprises alkoxy, alkyl-thio, alkyl-thio-alkyl, alkoxyalkyl, alkylamino, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Preferably, the alkyl group has 1 to 12 carbons. More preferably it is a lower alkyl of from 1 to 7 carbons, more preferably 1 to 4 carbons. The alkyl group can be substituted or unsubstituted.

When substituted, the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkenyl groups containing at least one carbon-carbon double bond, including straight-chain, branched-chain, and cyclic groups. Preferably, the alkenyl group has 2 to 12 carbons. More preferably. it is a lower alkenyl of from 2 to 7 carbons, even more preferably 2 to 4 carbons. The alkenyl group can be substituted or unsubstituted. When substituted, the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkynyl groups containing at least one carbon-carbon triple bond, including straight-chain, branched-chain, and cyclic groups. Preferably, the alkynyl group has 2 to 12 carbons. More preferably it is a lower alkynyl of from 2 to 7 carbons, more preferably 2 to 4 carbons. The alkynyl group can be substituted or unsubstituted. When substituted, the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Alkyl groups or moieties of the invention can also include aryl, alkylaryl, carbocyclic aryl, heterocyclic aryl, amide and ester groups. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen. It is understood that, for convenience, the above-mentioned groups can all be included within the definition of "alkyl" for purposes of this application.

The term "alkanoyl" as used herein refers to an alkyl group attached to the parent molecular moiety through a carbonyl group.

The term "alkoxyalkyl" as used herein refers to an alkyl-O-alkyl ether, for example methoxyethyl or ethoxymethyl.

The term "alkyl-thio-alkyl" as used herein refers to an alkyl-S-alkyl thioether, for example methylthiomethyl or methylthioethyl.

The term "amino" as used herein refers to a nitrogen containing group as is known in the art derived from ammonia by the replacement of one or more hydrogen radicals by organic radicals. For example, the terms "aminoacyl" and "aminoalkyl" refer to specific N-substituted organic radicals with acyl and alkyl substituent groups respectively.

The term "silylating reagent" as used herein refers to a chemical reagent used to introduce a silyl group to a compound.

The term "alkenyl" as used herein refers to a straight or branched hydrocarbon of a designed number of carbon atoms containing at least one carbon-carbon double bond. Examples of "alkenyl" include vinyl, allyl, and 2-methyl-3-heptene.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkenyl" as used herein refers to a C3-C8 cyclic hydrocarbon containing at least one carbon-carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" as used herein refers to a C3-C8 cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C3-C7 cycloalkyl group attached to the parent molecular moiety through an alkyl group, as defined above. Examples of cycloalkylalkyl groups include cyclopropylmethyl and cyclopentylethyl.

The terms "halogen" or "halo" as used herein refers to indicate fluorine, chlorine, bromine, and iodine.

The term "heterocycloalkyl," as used herein, refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "C1-C6 hydrocarbyl" as used herein refers to straight, branched, or cyclic alkyl groups having 1-6 carbon atoms, optionally containing one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, cyclopropylmethyl, cyclopropyl, cyclohexylmethyl, cyclohexyl and propargyl. When reference is made herein to C1-C6 hydrocarbyl containing one or two double or triple bonds it is understood that at least two carbons are present in the alkyl for one double or triple bond, and at least four carbons for two double or triple bonds.

The term "nitrogen protecting group," as used herein, refers to groups known in the art that are readily introduced on to and removed from a nitrogen. Examples of nitrogen protecting groups include Boc, Cbz, benzoyl, and benzyl. See also "Protective Groups in Organic Synthesis", 3rd Ed., Greene, T. W. and related publications.

The term "5'-protected nucleoside" as used herein refers to a nucleoside bearing a 5'-protecting group, for example an acid labile protecting group such as a trityl, dimethoxytrityl, or monomethoxytrityl group.

The term "5'-protected N-protected nucleoside" as used herein refers to a 5'-protected nucleoside further comprising amino protection, for example exocylic amine protection such as acyl or amide protection or 2'-amino protection such as TFA or phthalimide protection.

The term "nucleotide" as used herein, refers to a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "nucleoside" as used herein, refers to a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, modified nucleosides, non-natural nucleosides, non-standard nucleosides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "abasic" as used herein, refers to sugar moieties lacking a base or having other chemical groups in place of a base at the 1' position, (for more details see Wincott et al., International PCT publication No. WO 97/26270).

The term "unmodified nucleoside" as used herein, refers to one of the bases adenine, cytosine, guanine, thymine, uracil joined to the 1' carbon of β-D-ribo-furanose.

The term "modified nucleoside" as used herein, refers to any nucleotide base which contains a modification in the chemical structure of an unmodified nucleotide base, sugar and/or phosphate.

The term "oligonucleotide" as used herein, refers to a molecule comprising two or more nucleotides. An oligonucleotide can comprise ribonucleic acids, deoxyribonucleic acids, and combinations and/or chemically modified derivatives thereof. Oligonucleotides can comprise nucleic acids such as enzymatic nucleic acids, antisense nucleic acids, aptamers, decoys, allozymes, ssRNA, double stranded RNA, siRNA, triplex oligonucleotides or 2,5-A chimeras.

The term "enzymatic nucleic acid molecule" as used herein refers to a nucleic acid molecule which has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50-75% can also be useful in this invention (see for example Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

The term "antisense nucleic acid", as used herein refers to a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review, see Stein and Cheng, 1993 *Science* 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to a substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, *J. Biol. Chem.*, 274, 21783-21789, Delihas et al., 1997, *Nature*, 15, 751-753, Stein et al., 1997, *Antisense N. A. Drug Dev.*, 7, 151, Crooke, 2000, *Methods Enzymol.*, 313, 3-45; Crooke, 1998, *Biotech. Genet. Eng. Rev.*, 15, 121-157, Crooke, 1997, *Ad. Pharmacol.*, 40, 1-49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

The term "RNase H activating region" as used herein refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see for example Arrow et al., U.S. Pat. No. 5,849,902; Arrow et al., U.S. Pat. No. 5,989,912). An RNase H enzyme binds to a nucleic acid molecule-target RNA complex and cleaves the target RNA sequence. An RNase H activating region comprises, for example, phosphodiester, phosphorothioate (preferably at least four of the nucleotides are phosphorothiote substitutions; more specifically, 4-11 of the nucleotides are phosphorothiote substitutions); phosphorodithioate, 5'-thiophosphate, or methylphosphonate backbone chemistry or a combination thereof. In addition to one or more backbone chemistries described above, an RNase H activating region can also comprise a variety of sugar chemistries. For example, an RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of an RNase H activating region and the instant invention.

The term "single stranded RNA" (ssRNA) as used herein refers to a naturally occurring or synthetic ribonucleic acid molecule comprising a linear single strand, for example a ssRNA can be a messenger RNA (mRNA), transfer RNA (tRNA), ribosomal RNA (rRNA) etc. of a gene.

The term "double stranded RNA" or "dsRNA" as used herein refers to a double stranded RNA molecule capable of RNA interference, including short interfering RNA (siRNA), see for example Bass, 2001, *Nature,* 411, 428-429; Elbashir et al., 2001, *Nature,* 411, 494-498)

The term "allozyme" as used herein refers to an allosteric enzymatic nucleic acid molecule, see for example see for example George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842.

The term "2-5A chimera" as used herein refers to an oligonucleotide containing a 5'-phosphorylated 2'-5'-linked adenylate residue. These chimeras bind to target RNA in a sequence-specific manner and activate a cellular 2-5A-dependent ribonuclease which, in turn, cleaves the target RNA (Torrence et al., 1993 *Proc. Natl. Acad. Sci. USA* 90, 1300; Silverman et al., 2000, *Methods Enzymol.,* 313, 522-533; Player and Torrence, 1998, *Pharmacol. Ther.,* 78, 55-113).

The term "triplex forming oligonucleotides" as used herein refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504; Fox, 2000, *Curr. Med. Chem.,* 7, 17-37; Praseuth et. al., 2000, *Biochim. Biophys. Acta,* 1489, 181-206).

The term "decoy " as used herein refers to a nucleic acid molecule, for example RNA or DNA, or aptamer that is designed to preferentially bind to a predetermined ligand. Such binding can result in the inhibition or activation of a target molecule. A decoy or aptamer can compete with a naturally occurring binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, Cell, 63, 601-608). This is but a specific example and those in the art will recognize that other embodiments can be readily generated using techniques generally known in the art, see for example Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628. Similarly, a decoy can be designed to bind to other proteins and block the binding of DNA or RNA to a nucleic acid binding protein, or a decoy can be designed to bind to proteins and prevent other molecular interactions with the protein.

Katzhendler et al., 1989, supra, also suggest that the optimal loading of 3'-terminal chemical groups onto the spacer molecules should range from 5-23.7 µmol per gram of solid support to achieve efficient DNA synthesis.

Applicant has surprisingly found that the loading of greater than 40 µmol of the 3'-terminal chemical group onto the spacer molecule, per gram of solid support allows for the efficient synthesis of oligonucleotides, including RNA oligonucleotides. Thus, in a one embodiment, this invention features the method for solid phase synthesis of oligonucleotides described in method A, wherein the terminal chemical group is loaded onto the solid support bound spacer molecule at a concentration greater than or equal to 40 µmol/gram of solid support and less than 100 µmol/gram, preferably 40, 45, 50, 55, 60, 65, 70, 75, 80, 90, and 100 µmol/gram of solid support.

The term "loading" as used herein, refers to the covalent attachment of a terminal chemical group, such as abasic succinate or another suitable chemical moiety onto the spacer molecule linked to the solid support. The terminal chemical group is either a protected initial nucleoside or any other chemical group that is attached at the 3'end of the oligonucleotide being synthesized. Loading generally occurs prior to the initiation of oligonucleotide synthesis.

DESCRIPTION OF THE PREFERRED EMBODIMENTS

The drawings will first briefly be described.

Drawings

FIG. 1 is a schematic representation of a process for synthesis of oligonucleotides using solid phase phosphoramidite chemistry. The process includes detritylation (A), coupling (B), oxidation (C), and capping (D), which are repeated until the oligonucleotide molecule is completely synthesized.

FIG. 2 displays examples of the spacers that can be used for the synthesis of oligonucleotides. In addition, product yields and reaction efficiencies for the synthesis of oligonucleotides are also included.

FIG. 3 shows an HPLC chromatograph of ribozyme synthesized using CPG linked HHDA spacer. The reaction was performed using controlled pore glass with loading of 56 µmol/g of abasic succinate and yielded 266 optical density units (ODU)/µmol of crude material.

FIG. 4 is shows the HPLC chromatographs of ribozymes synthesized on CPG-linker PEG and UDDA Spacers.

FIG. 5 is a non-limiting example of a chemical scheme for the synthesis of derivatized 22 atom CPG, HHDA spacer.

FIG. 6 is a non-limiting example of a chemical scheme for the synthesis of derivatized 19 atom CPG, PEG-CPG spacer.

FIG. 7 is a non-limiting example of a chemical scheme for the synthesis of derivatized 20 atom CPG, UDDA spacer.

Figure 1:
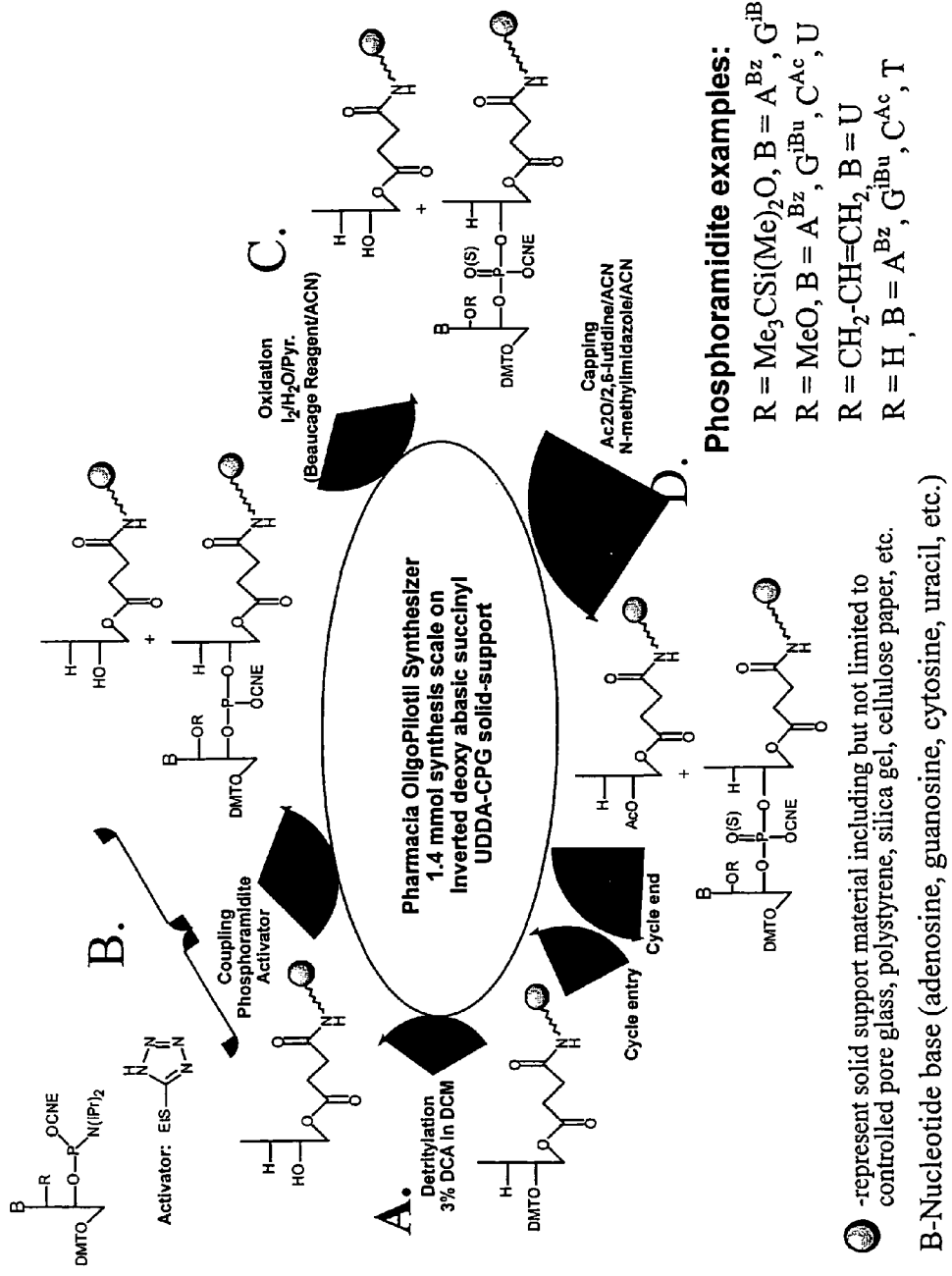

FIG. 8 displays examples of general formulas covered under the present invention. In formula a, X is an integer greater than or equal to 2 and less than or equal to 6. In formula b, Y is an integer greater than or equal to 1 and less than or equal to 4. In formula c, V is an integer greater than or equal to 5 and less than or equal to 16. In all of the formulae a-d, SP represents a solid support; where the solid support is select from a group including controlled pore glass; polystrene; silica gel; cellulose paper; polyamide/kieselgur; and polacryloylmorpholide; B represents the terminal chemical group such as abasic succinate, nucleotides, etc., where B can be linked to the growing RNA chain via 3'-5', 3'-2', or 3'-3' linkages; and R is independently a moiety selected from a group consisting of alkyl, alkenyl, alkynyl, aryl, alkylaryl, carbocyclic aryl, heterocyclic aryl, amide and ester.

FIG. 9 is a non-limiting example of a chemical scheme for the synthesis of derivatized 13 atom CPG, C9 spacer.

FIG. 10 shows a capillary gel electrophoresis (CGE) chromatogram of a crude 36-mer enzymatic nucleic acid synthesized on 13 atom CPG, C9 spacer with an inverted abasic terminal moiety.

FIG. 11 is a schematic representation of a process for synthesis of oligonucleotides using solid phase phosphoramidite chemistry. The process includes detritylation (A), 5'-activation (B), coupling (C), oxidation (D), and capping (E), which are repeated until the oligonucleotide molecule is completely synthesized.

OLIGONUCLEOTIDE SYNTHESIS

In one embodiment, the invention features a method (Method E) for the synthesis of oligonucleotides comprising: 5'-deblocking, 5'-activation, coupling, oxidation, and capping, wherein these steps are repeated under conditions suitable for the synthesis of an oligonucleotide, and wherein 5'-activation comprises the in situ formation of an activated 5'-phosphorus species and coupling comprises the nucleophilic attack of the activated 5'-phosphorus species under conditions suitable for covalent attachment of the nucleophile to the activated 5'-phosphorus species.

In another embodiment, the 5'-activation contemplated by the invention comprises the in situ formation of a nucleoside 5'-O-phosphoramidite. In yet another embodiment, the nucleoside 5'-O-phosphoramidite of the invention is 5'-O-nucleoside 2-cyanoethyl-N,N-diisopropylphosphoramidite.

In one embodiment, the 5'-activation contemplated by the invention comprises conjugation of a nucleoside 5'-hydroxyl with a phosphine in the presence of an activator. In another embodiment, the phosphine contemplated by the invention comprises cyanoethyl-(bis)-N,N-diisopropylphosphoramidite (2-cyanoethyl tetraisopropylphosphorodiamidite) and the activator comprises S-ethyl tetrazole (SET), tetrazole, or dicyanoimidazole (DCI).

In another embodiment, the method for the synthesis of oligonucleotides comprising: 5'-deblocking, 5'-activation, coupling, oxidation, and capping is a solid phase synthesis, solution phase synthesis, or mixed phase synthesis.

In yet another embodiment, solid phase synthesis via Method A of the invention is carried out on a solid support comprising silicon-based chips, controlled pore glass; polystyrene; nylon, silica gel; cellulose paper; polyamide/kieselgur; or polacryloylmorpholide.

In one embodiment, the conditions suitable for covalent attachment of the nucleophile to the activated 5'-phosphorus species in Method A of the invention comprises the use of an activator, or example S-ethyl tetrazole (SET), tetrazole, or dicyanoimidazole (DCI), in the presence of a 5'-protected or 5'-protected N-protected nucleoside bearing a nucleophile such as a hydroxyl group.

The compounds and methods of the invention are readily adapted for use with known synthetic protocols for oligonucleotide synthesis. In addition, the compounds and methods of the invention can be used to synthesize both naturally occurring and chemically modified nucleic acid polymers.

The method of oligonucleotide synthesis generally followed in the art is described by Usman et al., supra, Scaringe et al., *Nucleic Acids Res.* 1990, 18, 5433-5441, and Caruthers, U.S. Pat. No. 4,458,066, and makes use of common nucleic acid protecting and coupling groups, such as dimethoxytrityl at the 5'-end, and phosphoramidites at the 3'-end. Alternately, Method E of the invention is used, wherein an activated phosphorus species is generated in situ before coupling with the incoming nucleoside. Those skilled in the art will recognize that other protecting and coupling groups can be used for solid phase oligonucleotide synthesis and are hence within the scope of the invention. A more detailed description of oligonucleotide synthesis follows.

Solid support and spacer selection: Prior to the initiation of oligonucleotide synthesis, a proper solid support and spacer is selected. A number of different inorganic polymers can be utilized for the solid phase synthesis of oligonucleotides including silica, aluminosilicates, borosilicates, porous glass, metal oxides, and clays. The type of solid support is often chosen based on the length of the oligonucleotide to be synthesized. The support is preferably comprised of a uniform surface with pores large enough to accommodate the oligonucleotide of interest (e.g. 300-2000 Å). Additional preferable characteristics of the support include particle size (40-500 mesh), bulk density (0.1-1.0 g/cc), SS. Area (10-200 $M^2$/g), and pore volume (0.2-3.0 cc/g). In a preferred embodiment, the solid support is comprised of controlled pore glass (CPG) with a pore size of about 630 Å, a particle size of about 120 to 200 mesh, a bulk density of about 0.24 g/cc, a SS. Area of about 77 $M^2$/g, and a pore volume of about 1.8 cc/g. In addition, the support contains a minimum number of additional surface chemical groups that can react to produce undesired products and thus lower yield.

The molecular characteristics of the spacer are expected to have a significant effect on the efficiency of oligonucleotide synthesis. The synthesis of oligonucleotides occurs in close proximity to the surface of the solid support and therefore, the length and type of spacer used can be a critical variable (Pon, supra). Contrary to the published literature, applicant believes that the chemistry of the spacer can be more important than the length of the spacer. A spacer with chemistry that promotes the extension rather than contraction of the spacer chain can have a greater probability of supporting efficient synthesis of oligonucleotides. The quantity of initial nucleotide or chemical moiety loaded onto the solid support can also play a role in the efficiency of oligonucleotide synthesis. Efficient synthesis of DNA oligonucleotides has been reported at a loading of between 5.5-24 µmol spacer per gram of solid support (Katzhendler et al., supra). Applicant believes that for the synthesis of oligonucleotides having RNA nucleotides, spacer loading can be increased to 40-100 µmol without a substantial decrease in the efficiency of oligonucleotide synthesis. Therefore, in one embodiment, the invention features a method for oligonucleotide synthesis where a derivatized solid support of the invention comprises a loading of 40-100 µmol.

In another embodiment, the invention features the use of an inline mixture upstream of the solid support used in a method of the invention. The inline mixer can allow for homogeneity of the phosphoramidite/activator solution prior to contact with the solid support, thereby resulting in complete phosphoramidite activation. In the absence of the inline mixer, the phosphoramidite/activator stream can have localized areas of a highly concentrated species or "plugs" consisting of either phosphoramidite or activator. The sequential exposure of the support to these "plugs" can result in the formation of N+x oligomers (x being any integer greater than or equal to 1) and/or other side reactions. Most notably, concentrated "plugs" of activator can deblock acid labile protecting groups resulting in undesirable polymerization events. Concentrated "plugs" of phosphoramidite lacking activator can result in the effective lowering of reactive equivalents, thereby compromising synthesis quality (N−1 events). The use of inline mixer is likely to improve the overall efficiency of oligonucleotide synthesis, quality of oligonucleotides synthesized and/or the overall yield of the oligonucleotide synthesized.

The term "inline mixer" as used herein refers to any type of mixer that is compatible with an oligonucleotide synthesis platform, provided that effective mixing of the desired components involved in the synthesis is enabled. An inline (pipeline) mixer can comprise any of the following types: Inline fixed element mixer, inline removable element mixer, inline edge sealed mixer, or inline high efficiency vortex mixer. In a specific example, the use of a Komax Systems Inc. Inline tube mixer, part number 375-027 is provided.

Synthesis of Oligonucleotides (phosphite-triester method): The trityl group (e.g. dimethoxytrityl) is removed from the initial nucleotide or non-nucleotide moiety (B in the above Formulae) on the spacer from either the 2', 3', or 5' end (FIG. 1A). Removal of the trityl group exposes a reactive hydroxyl group capable of binding to the next nucleoside. The next nucleoside, in the form of a phosphoramidite molecule is activated using reagents such as, but not limited to, tetrazole, S-ethyl tetrazole, and 4,5-dicyanoimidazole (DCI), and is attached to the initial nucleoside by an internucleotide phosphite-triester linkage (FIG. 1B). The phosphite-triester is then oxidized to yield a phophate bond which is the more stable internucleotide linkage (FIG. 1C).

Alternately, The trityl group (e.g. dimethoxytrityl) is removed from the initial nucleotide or non-nucleotide moiety (B in the above Formulae) on the spacer from either the 2', 3', or 5' end (FIG. 11A). Removal of the trityl group exposes a reactive hydroxyl group. The free hydroxyl is then coupled to a phosphine in the presence of an activator such as, but not limited to, tetrazole, S-ethyl tetrazole, and 4,5-dicyanoimidazole (DCI), to generate a reactive 5'-phosphorus species (FIG. 11B). The next nucleoside, in the form of a 5'-protected molecule bearing a free nucleophile, for example a 3'-hydroxyl, is attached to the initial nucleoside by an internucleotide phosphite-triester linkage (FIG. 11C). The phosphite-triester is then oxidized to yield a phophate bond which is the more stable internucleotide linkage (FIG. 11D)

Because the addition of activated phosphoramidites onto detritylated hydroxyl groups or addition of nucleophiles to 5'-activated phosphorus species usually does not proceed to 100% completion, these unreactive hydroxyl groups are capped to prevent the formation of undesired products. For example, acetic anhydride can be utilized to cap the spacer with an acetyl group (FIG. 1D). This capping step can optionally take place before or after the oxidation of the phosphite bond.

The steps described above, from detritylation to capping, is repeated until all of the desired nucleosides are added onto the growing oligonucleotide chain. The newly synthesized nucleic acid molecule is then ready for the removal of all existing protecting groups, for example phosphate ester protecting groups such as cyanoethyl protecting groups, base protecting groups such as acetyl, benzoyl and isobutyryl groups, and protecting groups from the 2' position of the nucleotides, such as tert-butyldimethylsilyl groups for ribonucleotides or phthaloyl groups for 2'-amino nucleosides.

In a non-limiting example, small scale synthesis of non-ribonucleotide (2'-OH) containing oligonucleotides are conducted on a 394 Applied Biosystems, Inc. synthesizer using a 0.2 μmol scale protocol with a 2.5 min coupling step for 2'-O-methylated nucleotides and a 45 sec coupling step for 2'-deoxy nucleotides. Table I outlines the amounts and the contact times of the reagents used in the synthesis cycle. Alternatively, syntheses at the 0.2 μmol scale can be performed on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. A 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include; detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyl tetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the oligonucleotide is performed as follows: the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for oligonucleotides comprising RNA nucleotides (2'-OH) and/or chemically modified RNA nucleotides including other modifications such as 2'-C-allyl nucleotides, 2'-amino nucleotides or 2'-O-amino nucleotides follows the procedure as described in Usman et al., 1987, *J. Am. Chem. Soc.*, 109, 7845; Scaringe et al., 1990, *Nucleic Acids Res.*, 18, 5433; and Wincott et al., 1995, *Nucleic Acids Res.* 23, 2677-2684 Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Table I outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by calorimetric quantitation of the trityl fractions, are typically 97.5-99%. Other oligonucleotide synthesis reagents for the 394 Applied Biosystems, Inc. synthesizer include; detrylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyl tetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA containing oligonucleotides is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA•3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 min. The vial is brought to r.t. TEA.3HF (0.1 mL) is added and the vial is heated at 65° C. for 15 min. The sample is cooled at −20° C. and then quenched with 1.5 M $NH_4HCO_3$.

In another non-limiting example, small scale synthesis of oligonucleotides are conducted on a 394 Applied Biosystems, Inc. synthesizer according to Method E of the invention using a 0.2 μmol scale protocol. A 2-10 minute activation time is used to couple cyanoethyl-(bis)-N,N-diisopropylethyl phosphoramidite (2-cyanoethyl tetraisopropylphosphorodiamidite) (1.1-10 equivalents) to a free terminal hydroxyl group in the presence of 1.1-10 equivalents of SET. This is followed by a 1-10 min coupling step for 5'-protected nucleotides in the presence of additional SET (1-10 equivalents). The remainder of the synthesis cycle is performed according to the examples above.

Purification: The most quantitative procedure for recovering the fully deprotected oligonucleotide is by either ethanol precipitation, or an anion exchange cartridge desalting, as described in Scaringe et al. *Nucleic Acids Res.* 1990, 18, 5433-5341. The purification of long oligonucleotide sequences can be accomplished by a two-step chromatographic procedure in which the oligonucleotide is first purified on a reverse phase column with either the trityl group at the 5' position on or off. This purification is accomplished using an acetonitrile gradient with triethylammonium or bicarbonate salts as the aqueous phase. In the case of the trityl on purification, the trityl group can be removed by the addition of an acid and drying of the partially purified oligonucleotide molecule. The final purification is carried out on an anion exchange column, using alkali metal perchlorate salt gradients to elute the fully purified oligonucleotide molecule as the appropriate metal salts, e.g. $Na^+$, $Li^+$ etc. A final desalting step on a small reverse-phase cartridge completes the purification procedure.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 min. The cartridge is then washed again with water, salt exchanged with 1 M NaCl and washed with water again. The oligonucleotide is then eluted with 30% acetonitrile.

Applications

The methods of the present invention can be employed to synthesize highly pure samples of oligonucleotides which can be used for a number of applications. A great deal of effort has been placed on blocking or altering cellular processes such as transcription and translation for a variety of purposes, such as understanding biology, gene function, disease processes, and identifying novel therapeutic targets. Molecules capable of blocking these processes include but are not limited to enzymatic nucleic acid molecule, antisense molecules, 2-5A chimeras, decoys, siRNA, triplex oligonucleotides, and allozymes as described herein.

For example, enzymatic nucleic acid molecules can be synthesized which can inhibit gene expression in a highly specific manner by binding to and causing the cleavage of the mRNA corresponding to the gene of interest, and thereby prevent production of the gene product (Christoffersen, *Nature Biotech,* 1997, 2, 483-484).

By monitoring inhibition of gene expression and correlation with phenotypic results, the relative importance of the particular gene sequence to disease pathology can be established. The process can be both fast and highly selective, and allow for the process to be used at any point in the development of the organism.

Several varieties of naturally-occurring enzymatic RNAs are presently known. In addition, several in vitro selection (evolution) strategies (Orgel, 1979, *Proc. R. Soc. London,* B 205, 435) have been used to evolve new nucleic acid catalysts capable of catalyzing cleavage and ligation of phosphodiester linkages (Joyce, 1989, *Gene,* 82, 83-87; Beaudry et al., 1992, *Science* 257, 635-641; Joyce, 1992, *Scientific American* 267, 90-97; Breaker et al., 1994, *TIBTECH* 12, 268; Bartel et al., 1993, *Science* 261:1411-1418; Szostak, 1993, *TIBS* 17, 89-93; Kumar et al., 1995, *FASEB J.,* 9, 1183; Breaker, 1996, *Curr. Op. Biotech.,* 7, 442; Santoro et al., 1997, *Proc. Natl. Acad. Sci.,* 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495; all of these are incorporated by reference herein). Each can catalyze a series of reactions including the hydrolysis of phosphodiester bonds in trans (and thus can cleave other RNA molecules) under physiological conditions. Nucleic acid molecules of this invention will block to some extent gene and protein expression and can be used to treat disease or diagnose disease associated with the levels of disease related genes and/or proteins.

The enzymatic nature of an enzymatic nucleic acid molecule can allow the concentration of enzymatic nucleic acid molecule necessary to affect a therapeutic treatment to be lower than a nucleic acid molecule lacking enzymatic activity, such as an antisense nucleic acid. This reflects the ability of the enzymatic nucleic acid molecule to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of a enzymatic nucleic acid molecule.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieve efficient cleavage in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, *Einstein Quart. J. Bio. Med.,* 6, 92; Haseloff and Gerlach, 334 *Nature* 585, 1988; Cech, 260 *JAMA* 3030, 1988; and Jefferies et al., 17 *Nucleic Acids Research* 1371, 1989; Santoro et al., 1997 supra).

Because of their sequence specificity, trans-cleaving enzymatic nucleic acid molecules can be used as therapeutic agents for human disease (Usman & McSwiggen, 1995 *Ann. Rep. Med. Chem.* 30, 285-294; Christoffersen and Marr, 1995 *J. Med. Chem.* 38, 2023-2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited (Warashina et al., 1999, *Chemistry and Biology,* 6, 237-250).

Enzymatic nucleic acid molecules of the invention that are allosterically regulated ("allozymes") can be used to down-regulate gene expression. These allosteric enzymatic nucleic acids or allozymes (see for example George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842) are designed to respond to a signaling agent, for example, a mutant protein, wild-type protein, mutant RNA, wild-type RNA, other proteins and/or RNAs involved in a disease or infection, which in turn modulates the activity of the enzymatic nucleic acid molecule. In response to interaction with a predetermined signaling agent, the allosteric enzymatic nucleic acid molecule's activity is activated or inhibited such that the expression of a particular target is selectively down-regulated. In a specific example, allosteric enzymatic nucleic acid molecules that are activated by interaction with a RNA encoding a pathogenic protein are used as therapeutic agents in vivo. The presence of RNA encoding the pathogenic protein activates the allosteric enzymatic nucleic acid molecule that subsequently cleaves the RNA encoding the protein resulting in the inhibition of protein expression. In this manner, cells that express the pathogenic protein are selectively targeted.

In another non-limiting example, an allozyme can be activated by a protein, peptide, or mutant polypeptide that caused the allozyme to inhibit the expression of a gene, by, for example, cleaving RNA encoded by the gene. In this non-limiting example, the allozyme acts as a decoy to inhibit the function of a protein and also inhibit the expression of protein once activated by the protein.

Antisense molecules can be modified or unmodified RNA, DNA, or mixed polymer oligonucleotides and primarily function by specifically binding to matching sequences resulting in inhibition of peptide synthesis (Woo-Pong, November 1994, *BioPharm*, 20-33). The antisense oligonucleotide binds to target RNA by Watson Crick base-pairing and blocks gene expression by preventing ribosomal translation of the bound sequences either by steric blocking or by activating RNase H enzyme. Antisense molecules can also alter protein synthesis by interfering with RNA processing or transport from the nucleus into the cytoplasm (Mukhopadhyay & Roth, 1996, *Crit. Rev. in Oncogenesis* 7, 151-190).

In addition, binding of single stranded DNA to RNA can result in nuclease degradation of the heteroduplex (Woo-Pong, supra; Crooke, supra). To date, the only backbone modified DNA chemistry which act as substrates for RNase H are phosphorothioates, phosphorodithioates, and borontrifluoridates. Recently it has been reported that 2'-arabino and 2'-fluoro arabino-containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526; Thompson et al., International PCT Publication No. WO 99/54459; Hartmann et al., U.S. Ser. No. 60/101,174, filed on Sep. 21, 1998). All of these references are incorporated by reference herein in their entirety.

In addition, antisense deoxyoligoribonucleotides can be used to target RNA by means of DNA-RNA interactions, thereby activating RNase H, which digests the target RNA in the duplex. Antisense DNA can be expressed via the use of a single stranded DNA intracellular expression vector or equivalents and variations thereof.

Single stranded DNA can be designed to bind to genomic DNA in a sequence specific manner. Triplex Forming Oligonucleotides (TFOs) are comprised of pyrimidine-rich oligonucleotides which bind DNA helices through Hoogsteen Base-pairing. The resulting triple helix composed of the DNA sense, DNA antisense, and TFO disrupts RNA synthesis by RNA polymerase. The TFO mechanism can result in gene expression or cell death since binding can be irreversible (Mukhopadhyay & Roth, supra).

The 2-5A system is an interferon-mediated mechanism for RNA degradation found in higher vertebrates (Mitra et al., 1996, *Proc Nat Acad Sci USA* 93, 6780-6785). Two types of enzymes, 2-5A synthetase and RNase L, are required for RNA cleavage. The 2-5A synthetases require double stranded RNA to form 2'-5' oligoadenylates (2-5A). 2-5A then acts as an allosteric effector for utilizing RNase L which has the ability to cleave single stranded RNA. The ability to form 2-5A structures with double stranded RNA makes this system particularly useful for inhibition of viral replication.

(2'-5') oligoadenylate structures can be covalently linked to antisense molecules to form chimeric oligonucleotides capable of RNA cleavage (Torrence, supra). These molecules putatively bind and activate a 2-5A dependent RNase, the oligonucleotide/enzyme complex then binds to a target RNA molecule which can then be cleaved by the RNase enzyme. The covalent attachment of 2'-5' oligoadenylate structures is not limited to antisense applications, and can be further elaborated to include attachment to nucleic acid molecules of the instant invention.

Targets for useful enzymatic nucleic acid molecules and antisense nucleic acids can be determined as disclosed in Draper et al., WO 93/23569; Sullivan et al., WO 93/23057; Thompson et al., WO 94/02595; Draper et al., WO 95/04818; McSwiggen et al., U.S. Pat. No. 5,525,468, and hereby incorporated by reference herein in totality. Other examples include the following PCT applications, which concern inactivation of expression of disease-related genes: WO 95/23225, WO 95/13380, WO 94/02595, incorporated by reference herein. Rather than repeat the guidance provided in those documents here, provided below are specific examples of such methods, not limiting to those in the art. Enzymatic nucleic acid molecules to such targets are designed as described in those applications and synthesized to be tested in vitro and in vivo, as also described. The sequences of human RNAs are screened for optimal enzymatic nucleic acid target sites using a computer-folding algorithm. While human sequences can be screened and enzymatic nucleic acid molecule and/or antisense thereafter designed, as discussed in Stinchcomb et al., WO 95/23225, mouse targeted enzymatic nucleic acid molecules can be useful to test efficacy of action of the enzymatic nucleic acid molecule and/or antisense prior to testing in humans.

Optimizing Activity of the Nucleic Acid Molecule of the Invention.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, *TIBS*. 17, 34; Usman et al., 1994, *Nucleic Acids Symp. Ser.* 31, 163; Burgin et al., 1996, *Biochemistry*, 35, 14090). Sugar modification of nucleic acid molecules have been extensively described in the art (see Eckstein et al., *International Publication* PCT No. WO 92/07065; Perrault et al. *Nature*, 1990, 344, 565-568; Pieken et al. *Science*, 1991, 253, 314-317; Usman and Cedergren, *Trends in Biochem. Sci.*, 1992, 17, 334-339; Usman et al. *International Publication* PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010; all of the references are hereby incorporated in their totality by reference herein). Such publications describe general methods and strategies to determine the location of incorporation of sugar, base and/or phosphate modifications and the like into enzymatic nucleic acid molecules without inhibiting catalysis. In view of such teachings, similar modifications can be used as described herein to modify the nucleic acid molecules of the instant invention.

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications that maintain or enhance activity are provided. Such nucleic acid molecules are also generally more resistant to nucleases than unmodified nucleic acid molecules. Thus, in a cell and/or in vivo the activity may not be significantly lowered. Therapeutic nucleic acid molecules delivered exogenously are optimally stable within cells until translation of the target RNA has been inhibited long enough to reduce the levels of the undesirable protein. This period of time varies between hours to days depending upon the disease state. Nucleic acid molecules are preferably resistant to nucleases in order to function as effective intracellular therapeutic agents. Improvements in the chemical synthesis of RNA and DNA (Wincott et al., 1995 *Nucleic Acids Res.* 23, 2677; Caruthers et al., 1992, *Methods in Enzymology* 211, 3-19 (incorporated by reference herein)) have expanded the ability to modify nucleic acid molecules by introducing nucleotide modifications to enhance their nuclease stability as described above.

Use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of patients with nucleic acid molecules can also include combinations of different types of nucleic acid molecules.

Therapeutic nucleic acid molecules (e.g., enzymatic nucleic acid molecules and antisense nucleic acid molecules) delivered exogenously are optimally stable within cells until translation of the target RNA has been inhibited long enough to reduce the levels of the undesirable protein. This period of time varies between hours to days depending upon the disease state. These nucleic acid molecules should be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In another embodiment, nucleic acid catalysts having chemical modifications that maintain or enhance enzymatic activity are provided. Such nucleic acids are also generally more resistant to nucleases than unmodified nucleic acid. Thus, in a cell and/or in vivo the activity of the nucleic acid may not be significantly lowered. As exemplified herein such enzymatic nucleic acids are useful in a cell and/or in vivo even if activity over all is reduced 10 fold (Burgin et al., 1996, *Biochemistry,* 35, 14090). Such enzymatic nucleic acids herein are said to "maintain" the enzymatic activity of an all RNA ribozyme or all DNA DNAzyme.

In another aspect the nucleic acid molecules comprise a 5' and/or a 3'-cap structure.

The term "cap structure" as used herein refers to chemical modifications, which have been incorporated at either terminus of the oligonucleotide (see for example Wincott et al., WO 97/26270, incorporated by reference herein). These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

In another embodiment the 3'-cap includes, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

The term "non-nucleotide", "non-nucleoside" or "non-nucleosidic" as used herein refers to any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenine, guanine, cytosine, uracil or thymine.

In one embodiment, the invention features modified enzymatic nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, *Nucleic Acid Analogues: Synthesis and Properties*, in *Modern Synthetic Methods,* VCH, 331-417, and Mesmaeker et al., 1994, *Novel Backbone Replacements for Oligonucle-* otides, in *Carbohydrate Modifications in Antisense Research*, ACS, 24-39. These references are hereby incorporated by reference herein.

In connection with 2'-modified nucleotides as described for the present invention, by "amino" is meant 2'-$NH_2$ or 2'-O—$NH_2$, which can be modified or unmodified. Such modified groups are described, for example, in Eckstein et al., U.S. Pat. No. 5,672,695 and Matulic-Adamic et al., WO 98/28317, respectively, which are both incorporated by reference in their entireties.

Various modifications to nucleic acid (e.g., antisense and enzymatic nucleic acid molecule) structure can be made to enhance the utility of these molecules. For example, such modifications can enhance shelf life, half-life in vitro, stability, and ease of introduction of such oligonucleotides to the target site, including e.g., enhancing penetration of cellular membranes and conferring the ability to recognize and bind to targeted cells.

Use of these molecules can lead to better treatment of the disease progression by affording the possibility of combination therapies (e.g., multiple enzymatic nucleic acid molecules targeted to different genes, enzymatic nucleic acid molecules coupled with known small molecule inhibitors, or intermittent treatment with combinations of enzymatic nucleic acid molecules (including different enzymatic nucleic acid molecule motifs) and/or other chemical or biological molecules). The treatment of patients with nucleic acid molecules can also include combinations of different types of nucleic acid molecules. Therapies can be devised which include a mixture of enzymatic nucleic acid molecules (including different enzymatic nucleic acid molecule motifs), antisense and/or 2-5A chimera molecules to one or more targets to alleviate symptoms of a disease.

Diagnostic Uses

The nucleic acid molecules of this invention (e.g., ribozymes) can be used as diagnostic tools to examine genetic drift and mutations within diseased cells or to detect the presence of RNA in a cell. The close relationship between enzymatic nucleic acid molecule activity and the structure of the target RNA allows the detection of mutations in any region of the molecule which alters the base-pairing and three-dimensional structure of the target RNA. By using multiple enzymatic nucleic acid molecules described in this invention, one can map nucleotide changes which are important to RNA structure and function in vitro, as well as in cells and tissues. Cleavage of target RNAs with enzymatic nucleic acid molecules can be used to inhibit gene expression and define the role (essentially) of specified gene products in the progression of disease. In this manner, other genetic targets can be defined as important mediators of the disease. These experiments will lead to better treatment of the disease progression by affording the possibility of combinational therapies (e.g., multiple enzymatic nucleic acid molecules targeted to different genes, enzymatic nucleic acid molecules coupled with known small molecule inhibitors, or intermittent treatment with combinations of enzymatic nucleic acid molecules and/or other chemical or biological molecules). Other in vitro uses of enzymatic nucleic acid molecules of this invention are well known in the art, and include detection of the presence of mRNAs associated with a disease-related condition. Such RNA is detected by determining the presence of a cleavage product after treatment with an enzymatic nucleic acid molecule using standard methodology.

In a specific example, enzymatic nucleic acid molecules which can cleave only wild-type or mutant forms of the target RNA are used for the assay. The first enzymatic nucleic acid molecule is used to identify wild-type RNA present in the sample and the second enzymatic nucleic acid molecule will be used to identify mutant RNA in the sample. As reaction controls, synthetic substrates of both wild-type and mutant RNA can be cleaved by both enzymatic nucleic acid molecules to demonstrate the relative enzymatic nucleic acid molecule efficiencies in the reactions and the absence of cleavage of the "non-targeted" RNA species. The cleavage products from the synthetic substrates can also serve to generate size markers for the analysis of wild-type and mutant RNAs in the sample population. Thus each analysis can involve two enzymatic nucleic acid molecules, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential usefulness of sequence-specific enzymatic nucleic acid molecules of the instant invention might have many of the same applications for the study of RNA that DNA restriction endonucleases have for the study of DNA (Nathans et al., 1975 *Ann. Rev. Biochem.* 44:273). For example, the pattern of restriction fragments could be used to establish sequence relationships between two related RNAs, and large RNAs could be specifically cleaved to fragments of a size more useful for study. The ability to engineer sequence specificity of the enzymatic nucleic acid molecule is ideal for cleavage of RNAs of unknown sequence. Applicant describes the use of nucleic acid molecules to down-regulate gene expression of target genes in bacterial, microbial, fungal, viral, and eukaryotic systems including plant, or mammalian cells.

EXAMPLES

The following are non-limiting examples showing the synthesis of spacers of the present invention and their use for the synthesis of oligonucleotides and the use of an inline mixer for the improvement of oligonucleotide synthesis.

Example 1

Synthesis of 20 Atom CPG (Controlled Pore Glass), Urea-dodecylamine (UDDA)

p-Nitrophenyl chloroformate (4.8 g, 23 mmol) was dissolved in a mixture of $CH_2Cl_2$ (150 ml) and anhydrous pyridine (20 ml) (FIG. 7). Aminopropyl CPG (20 g, Prime Synthesis, 631 A°, Amine loading 180 µmoles/g), which was the chosen solid support material, was then added to this solution and the mixture was gently rotated for 3-4 hours at room temperature. The support was then filtered, washed with $CH_2Cl_2$ several times, followed by treatment with ether and dried. 20 mg of the solid support was submitted for loading test (described below) carried out by the addition of 0.2M NaOH (20 ml). The p-nitrophenolate anion liberated was monitored at 400 nm (e=17,000). The concentration of p-nitrophenolate onto this support was 200 µmole/gram of CPG.

Capping: Unreacted amine was capped by reacting the support with acetic anhydride/pyridine (100 ml, 1:1) for 30 minutes. The support was filtered, washed several times with $CH_3CN$, $CH_2Cl_2$ and ether and dried.

The spacer, 1,12-Dodecyldiamine (1.45 g, 7.25 mmol) was dissolved in $CH_2Cl_2$ (100 ml) and dry pyridine (10 ml). Solid support from the previous step was added to this solution and the yellow mixture was shaken gently overnight. The support was then filtered, sequentially washed several times with $CH_3OH$, $CH_3CN$, $CH_2Cl_2$ and ether and dried under reduced pressure. Diamine loading was quantitative.

Loading: The UDDA CPG support, was derivatized in $CH_2Cl_2$ (100 ml) by the sequential loading of 3'-O-Dimethoxytritylabasic-5'-succinate (abasic succinate) (1.34 g, 2.16 mmoles) (terminal oligoribonucleotide group), diisopropylcarbodiimide (0.5ml) and DMAP (0.4g) which were then allowed to rotate very slowly at room temperature for 3 hours. The support was then filtered, washed with $CH_3CN$, $CH_2Cl_2$ and ether and dried.

Abasic succinate loading was assayed by determining the amount of dimethoxytrityl cation released by acidic treatment of a sample of the support. An aliquot of approximately 10 mg of the derivatized support was weighed, and then reacted with perchloric acid solution (10 ml, 70% $HClO_4$ 51.4 ml+MeOH 46 ml). The absorbance of the compound was measured at 498 nm and the amount of bound linker in umol/g of support, was determined by using the following formula:

$$\frac{\text{Absorbance at } 498 \text{ nm} \times \text{vol (ml) of } HClO_4 \text{ } soln \times 14.3}{\text{wt of support (mg)}}$$

Using the above measurements, the linker loading was determined to be 65 µmol/g.

The unreacted amines were capped with acetontrile (100 ml) containing 2,6-lutidine (5 ml), acetic anhydride (5 ml) and NMI (20 ml) for 3 min. The support was filtered, washed with $CH_3OH$, $CH_3CN$, $CH_2Cl_2$ and ether and dried. The loading of the support was 58-60 µmole/g. The chemical structure of the UDDA spacer is shown in FIG. 2.

Example 2

Synthesis of 19 Atom CPG, PEG-CPG

Tetraethylene glycol CPG support was prepared by following the same procedure as described in example 1, but tetraethyleneglycol diamine was used as the starting material rather than 1,12-dodecyl diamine. The chemical reactions are shown in FIG. 6. Final abasic loading on this support was 50 µmoles/g. The chemical structure for the PEG spacer is shown in FIG. 2.

Tetraethyleneglycol diamine was synthesized in two steps from tetraethyleneglycol ditosylate. The ditosylate (50 g, 99.5 mmoles) was dissolved in dry DMF (250 ml) and sodium azide (19.5 g, 350 mmoles) was added. The reaction mixture was heated at 100° C. for 16 h. The mixture was concentrated and then triturated with $CH_2Cl_2$. The solid was filtered, washed several times with $CH_2Cl_2$ and the combined washings was evaporated to dryness under reduced pressure. The product, tetraethyleneglycol diazide was distilled under vacuum at 180° C. bath temperature. The protocol gave a product yield of 93%.

This compound was hydrogenated using $H_2$/10% Pd/C (800mg) in ethylacetate (150 ml). The catalyst was filtered, washed with ethylacetate and dried ($MgSO_4$). Evaporation of the solvent under reduced pressure afforded the diamine in 97% yield.

Example 3

Synthesis of 22 Atom CPG, HHDA

16-Hydroxyhexadecanoic acid (10. 112g, 37. 12 mmol) was coevaporated with dry pyridine (3×30 ml) and then dissolved in dry pyridine (100 ml) (FIG. 5). To this stirred ice cold mixture, a solution of DMTCl (16.35 g, 48.25 mmoles) in dry pyridine (100 ml) was added dropwise and the reaction mixture was allowed to stir at room temperature overnight. The reaction mixture was then cooled to 0° C., a solution of pentafluorophenol (9.56g, 51.97 mmol) dissolved in a mixture of $CH_2Cl_2$ (50 ml) and pyridine (15 ml) was added drop-wise to the reaction mixture with stirring. After another hour, dicyclohexylcarbodiimide (10.72 g, 51.97 mmol) in $CH_2Cl_2$ (70 ml) was added dropwise and the reaction mixture was left stirring at room temperature overnight. Precipitated N,N-dicyclohexylurea was filtered and the residue was washed with $CH_2Cl_2$. The combined washings was evaporated to dryness, redissolved in $CH_2Cl_2$ (200 ml), washed with 5% $NaHCO_3$ (100 ml) and dried over $Na_2SO_4$. The crude product was used as such for the next reaction.

To a solution of the above ester (0.7g), in a mixture of dry THF (50 ml) and dry pyridine (5 ml), aminopropyl CPG amine (10g, Prime Synthesis, pore size 630 A°, bulk density 0.26 g/cc, specific surface area 86.6 m²/g, pore volume 1.68 cc/g, particle size 80-200 mesh, initial loading 174 umol/g) was added slowly. The mixture was rotated very gently for a day and the solid was filtered, washed with $CH_3CN$ and $CH_2Cl_2$, dried in air and then under high vacuum.

The addition of the linker was assayed by determining the amount of dimethoxytrityl cation released by acidic treatment of a sample of the support, as mentioned earlier. The addition of N,N-dicyclohexylurea was found to be 85-90 umol/g. Subsequent capping and loading of abasic succinate was performed as in example 1. The loading of abasic succinate was calculated using the formula described above, which was 56 µmol/g. The chemical structure of 22 atom CPG, HHDA is given in FIG. 2.

Example 4

Synthesis of 13 Atom CPG, C9

Native CPG was silanized with N-(6-aminohexyl)aminopropyl trimethoxy silane according to the following procedure. CPG (2L) was suspended in a 3% solution of N-(6-aminohexyl)aminopropyl trimethoxy silane in anhydrous toluene (4L) and the mixture refluxed for 8-12 hours with slow stirring. The cooled suspension was then filtered and the support washed with toluene and dried under reduced pressure.

Loading (FIG. 9): The C9 CPG support, was derivatized in $CH_2Cl_2$ (100 ml) by the sequential loading of 3'-O-Dimethoxytritylabasic-5'-succinate (abasic succinate) (1.34g, 2.16 mmoles) (terminal oligoribonucleotide group), diisopropylcarbodiimide (0.5ml) and DMAP (0.4g) which were then allowed to rotate very slowly at room temperature for 3 hours. The support was then filtered, washed with $CH_3CN$, $CH_2Cl_2$ and ether and dried.

Abasic succinate loading was assayed by determining the amount of dimethoxytrityl cation released by acidic treatment of a sample of the support. An aliquot of approximately 10 mg of the derivatized support was weighed, and then reacted with perchloric acid solution (10 ml, 70% $HClO_4$ 51.4 ml+MeOH 46 ml). The absorbance of the compound was measured at 498 nm and the amount of bound linker in umol/g of support, was determined by using the following formula:

$$\frac{\text{Absorbance at } 498 \text{ nm} \times \text{vol (ml) of } HClO_4 \; soln \times 14.3}{\text{wt of support (mg)}}$$

Using the above measurements, the linker loading was determined to be 75 µmol/g.

The unreacted amines were capped with acetontrile (100 ml) containing 2,6-lutidine (5 ml), acetic anhydride (5 ml) and NMI (20 ml) for 3 min. The support was filtered, washed with $CH_3OH$, $CH_3CN$, $CH_2Cl_2$ and ether and dried. The loading of the support was 58-60 µmole/g. The chemical structure of the UDDA spacer is shown in FIG. 2.

Example 5

Synthesis of Ribozyme

A ribozyme having the sequence: $g_s a_s g_s u_s$ugcUGAuGag-gccgaaaggccGaaAgucugB (Angiozyme™) (SEQ ID NO: 1) was prepared on UDDA, PEG, and HDDA spacers linked to CPG, where g, a, u and c stands for 2'-O-methyl guanosine, adenosine, uridine, and cytidine respectively, U stands for 2'-C-allyl uridine, A and G stands for adenosine and guanosine respectively, s stands for phosphorothioate linkages and B stands for 3'-3' inverted abasic moiety. The synthesis was carried out on Pharmacia OligoPilot II automated synthesizer using 5'-DMT-2'-O-methyl-$N^2$-tert-butyl-phenoxy-acetylguanosine and 5'-DMT-2'-O-methyl-$N^6$-tert-butylphenoxyacetyl-adenosine, DMT-2'-O-TBDMS-$N^6$-tert-butylphenoxy-acetyl-adenosine 3'-N,N-diisopropyl-(2-cyanoethyl) phosphoramidites and 2'-O-metyl-5'-DMT-$N^4$-acetylcytidine, 2'-O-methyl-5'-DMT-uridine, 2'-C-allyl-5'-DMT-uridine 3'-N,N-diisopropyl-(2-cyanoethyl)-phosphoramidites. The synthesis cycle was as follows. The activator, 5-(ethylthio)-1H-tetrazole was formulated as 0.5M solution in $CH_3CN$ and phosphoramidite was formulated as 0.15M solution in $CH_3CN$. The syntheses were carried out using controlled pore glass (CPG) support of 600 Å pore size, 80-120 mesh, and 50-60 µmol/g loading with 5'-abasic succinate. Conditions for each step of synthesis is given in Table II.

Detritylation was achieved using Dichloroacetic acid in $CH_2Cl_2$ (3% v/v, Burdick & Jackson), the amounts used were determined by conductivity feedback, followed by 1.5 column volumes of $CH_3CN$ as a wash and another 1.5 column volumes of the detritylation solution. During the coupling step, 1.5 equivalents of nucleoside phosphoramidite was used for coupling of 2'-O-methyl (for 10 minutes) or 2.1 equivalents of nucleoside phosphoramidite was used for 2'-OH or 2'-C-allyl coupling (20 minutes). Equivalents are based on the moles of CPG bound 3'-terminal nucleoside. 8 equivalents of S-ethyl tetrazole (activator) was used to activate the phosphoramidites. Activator equivalents were based on molecules of nucleoside phosphoramidite. Oxidation of the phosphite bond to phosphate bond was accomplished using 0.05 M $I_2$ in 90:10 pyridine:water (Burdick & Jackson) with a contact time of 1 minute. Phosphorothioate internucleotide linkages were synthesized by sulfurization with 0.5 M Beaucage reagent for 3 minutes. And finally capping was achieved by using 6.3 equivalents of cap A (20% N-methyl imidazole, 80% $CH_3CN$) or 9.0 equivalents of cap B (20% acetic anhydride, 30% 2,6-lutidine, 50% $CH_3CN$).

The last trityl was left on the solid support. The support was dried and suspended in 1:1 33% methylamine/EtOH:dry DMSO (160 ml) and the mixture was allowed to shake at room temperature for 90 minutes. The reaction mixture was then quickly filtered, washed with dry DMSO (4×15 ml) and the combined washings was transferred to a Schott bottle. The solution was then cooled at −78° C. for a short time and to this cool solution TEA.3HF (80 ml) was added slowly. The reaction mixture was allowed to shake at 65° C. for 1 h in an incubated shaker. The bottle was then removed and cooled at −78° C. till the solution became a frozen slurry. 1.5M ammonium bicarbonate solution was then slowly added to the reaction mixture with periodic mixing. The material is then quantitated by UV at 260 nm and analyzed by HPLC. The HPLC chromatograph for ribozyme synthesized on CPG linked HHDA spacer is shown in FIG. 3. The absorbance for the product was 240 optical density units (ODU)/µmol of the crude reaction. The results for ribozyme synthesized on CPG linked UDDA and PEG spacer is shown in FIG. 4. The ribozyme on the PEG spacer and the UDDA spacer yield 290 and 266 ODU per µmol of crude reaction, respectively. A similar synthesis run on a 150 mmol scale using 3 equivalents of S-ethyl tetrazole (activator) resulted in 83% full length ribozyme based on CGE analysis of crude deprotected material.

Example 6

Synthesis of Ribozyme using 13 Atom CPG, C9

A ribozyme having the sequence: $g_s a_s g_s u_s$ugcUGAuGag-gccgaaaggccGaaAgucugB (Angiozyme™) (SEQ ID NO: 1) was prepared on the 13 atom CPG C9 spacer on a 200 umol scale, where g, a, u and c stands for 2'-O-methyl guanosine, adenosine, uridine, and cytidine respectively, U stands for 2'-C-allyl uridine, A and G stands for adenosine and guanosine respectively, s stands for phosphorothioate linkages and B stands for 3'-3' inverted abasic moiety. The synthesis was carried out on Pharmacia OligoPilot II or AKTA automated synthesizer using 5'-DMT-2'-O-methyl-$N^2$-isobutyryl guanosine, 5'-DMT-2'-O-methyl-$N^6$-benzoyl adenosine, 3'-N,N-diisopropyl-(2-cyanoethyl) phosphoramidites and 2'-O-metyl-5'-DMT-$N^4$-acetylcytidine, 2'-O-methyl-5'-DMT-uridine, 2'-C-allyl-5'-DMT-uridine 3'-N,N-diisopropyl-(2-cyanoethyl)-phosphoramidites. The synthesis cycle was as follows. The activator, 5-(ethylthio)-1H-tetrazole was formulated as 0.5M solution in $CH_3CN$ and phosphoramidite was formulated as 0.15M solution in $CH_3CN$. The syntheses were carried out using controlled pore glass (CPG) support of 600 Å pore size, 80-120 mesh, and 50-60 µmol/g loading with 5'-abasic succinate using the 13 atom C9 linker of the invention.

Detritylation was achieved using Dichloroacetic acid in $CH_2Cl_2$ (3% v/v, Burdick & Jackson), the amounts used were determined by conductivity feedback, followed by 1.5 column volumes of $CH_3CN$ as a wash and another 1.5 column volumes of the detritylation solution. During the coupling step, 1.5 equivalents of nucleoside phosphoramidite was used for coupling of 2'-O-methyl (for 10 minutes) or 2.1 equivalents of nucleoside phosphoramidite was used for 2'-OH or 2'-C-allyl coupling (20 minutes). Equivalents are based on the moles of CPG bound 3'-terminal nucleoside. 8 equivalents of S-ethyl tetrazole (activator) was used to activate the phosphoramidites. Activator equivalents were based on molecules of nucleoside phosphoramidite. Oxidation of the phosphite bond to phosphate bond is accomplished using 0.05 M $I_2$ in 90:10 pyridine:water (Burdick & Jackson) with a contact time of 1 minute. Phosphorothioate internucleotide linkages were synthesized by sulfurization with 0.5 M Beaucage reagent for 3 minutes. And finally capping was achieved by using 6.3 equivalents of cap A (20% N-methyl imidazole, 80% $CH_3CN$) or 9.0 equivalents of cap B (20% acetic anhydride, 30% 2,6-lutidine, 50% $CH_3CN$).

The last trityl was left on the solid support. The support was dried and suspended in 1:1 33% methylamine/EtOH:dry DMSO (160 ml) and the mixture was allowed to shake at room temperature for 90 minutes. The reaction mixture was then quickly filtered, washed with dry DMSO (4×15 ml) and the combined washings was transferred to a Schott bottle. The solution was then cooled at −78° C. for a short time and to this cool solution TEA.3HF (80 ml) was added slowly. The reaction mixture was allowed to shake at 65° C. for 1 h in an incubated shaker. The bottle was then removed and cooled at −78° C. till the solution became a frozen slurry. 1.5M ammonium bicarbonate solution was then slowly added to the reaction mixture with periodic mixing. The material was then quantitated by UV at 260 nm and analyzed by CGE. The CGE chromatograph for ribozyme synthesized on CPG linked C9 spacer is shown in FIG. 10. This synthesis on the C9 spacer provided 212 ODU per μmol of crude reaction.

Example 7

Synthesis of Ribozyme Using 13 Atom CPG, C9 Using Method E

A ribozyme having the sequence: $g_sa_sg_su_s$ugcUGAuGag-gccgaaaggccGaaAgucugB (Angiozyme™) (SEQ ID NO: 1) is prepared on the 13 atom CPG C9 spacer on a 200 umol scale according to Method E (see for example FIG. 11), where g, a, u and c stands for 2'-O-methyl guanosine, adenosine, uridine, and cytidine respectively, U stands for 2'-C-allyl uridine, A and G stands for adenosine and guanosine respectively, s stands for phosphorothioate linkages and B stands for 3'-3' inverted abasic moiety. The synthesis is carried out on Pharmacia OligoPilot II or AKTA automated synthesizer using 5'-DMT-2'-O-methyl-$N^2$-isobutyryl guanosine, 5'-DMT-2'-O-methyl-$N^6$-benzoyl adenosine, and 2'-O-metyl-5'-DMT-$N^4$-acetylcytidine, 2'-O-methyl-5'-DMT-uridine, 2'-C-allyl-5'-DMT-uridine nucleosides bearing a free 3'-hydroxyl. The synthesis cycle is as follows. The activator, 5-(ethylthio)-1H-tetrazole is formulated as 0.5M solution in $CH_3CN$ and phosphoramidite (2-cyanoethyl tetraisopropylphosphorodiamidite) is formulated as 0.15M solution in $CH_3CN$. The syntheses are carried out using controlled pore glass (CPG) support of 600 Å pore size, 80-120 mesh, and 50-60 μmol/g loading with 5'-abasic succinate using the 13 atom C9 linker of the invention.

Detritylation (step A, FIG. 11) is achieved using Dichloroacetic acid in $CH_2Cl_2$ (3% v/v, Burdick & Jackson), the amounts used are determined by conductivity feedback, followed by 1.5 column volumes of $CH_3CN$ as a wash and another 1.5 column volumes of the detritylation solution. The activation step (step B, FIG. 11) features the used of 2-cyanoethyl tetraisopropylphosphorodiamidite (2.0 equivalents) and 5-(ethylthio)-1H-tetrazole (8.0 equivalents) with a coupling time of 20 minutes per cycle. Following activation, coupling (step C, FIG. 11) of nucleoside (1.5 equivalents) in the presence of 5-(ethylthio)-1H-tetrazole (1.5 equivalents) takes place over an additional 20 minutes. Activator equivalents are based on molecules of nucleoside phosphoramidite. Oxidation (step D, FIG. 11) of the phosphite bond to phosphate bond is accomplished using 0.05 M $I_2$ in 90:10 pyridine: water (Burdick & Jackson) with a contact time of 1 minute. Phosphorothioate internucleotide linkages are synthesized by sulfurization with 0.5 M Beaucage reagent for 3 minutes. And finally capping (step E, FIG. 11) is achieved by using 6.3 equivalents of cap A (20% N-methyl imidazole, 80% $CH_3CN$) or 9.0 equivalents of cap B (20% acetic anhydride, 30% 2,6-lutidine, 50% $CH_3CN$).

The last trityl is left on the solid support. The support is dried and suspended in 1:1 33% methylamine/EtOH:dry DMSO (160 ml) and the mixture is allowed to shake at room temperature for 90 minutes. The reaction mixture is then quickly filtered, washed with dry DMSO (4×15 ml) and the combined washings are transferred to a Schott bottle. The solution is then cooled at −78° C. for a short time and to this cooled solution TEA.3HF (80 ml) is added slowly. The reaction mixture is allowed to shake at 65° C. for 1 h in an incubated shaker. The bottle is then removed and cooled at −78° C. till the solution became a frozen slurry. 1.5M ammonium bicarbonate solution is then slowly added to the reaction mixture with periodic mixing. The material is then quantitated by UV at 260 nm and analyzed by CGE.

Example 8

Incorporation of Inline Mixer

Introduction of inline mixer: Five experiments were performed at the 182 μmol scale. All syntheses were done using standard protected phosphoramidites (iBuG/BzA). The runs are summarized as follows: 8:1 (S-ethyl tetrazole) SET control (no mixer), 8:1 SET mixer, 6:1 control, 6:1 mixer, and 8:1 mixer (p-50). The mixer used was 1.9mL inline mixer from Komax. Mixer placement was between port 4 and valve 5 in all mixer runs except the last run (p-50) were the mixer was placed between post-p-50 pump and valve 6. Control runs used no mixer. Phosphoramidite equivalent was 1.5/2.1 for 2'-O-Me/RNA for all syntheses. Results of all five syntheses are summarized in Table III a.

GMP inline mixer runs: Two experimental runs were done along with controls in the cGMP facility at the 3000 μmol scale. The first experimental run was done using the standard 2.1 phosphoramidite equivalents using an 8:1 ratio of SET with the 11.1 mL inline-mixer (port 4/valve 5). Standard 3000 μmol delivery styles were maintained in this run, including the 2× volume phosphoramidite approach for all bases.

The second experimental run was done using a modified coupling cycle with the 11.1 mL mixer (port 4/valve 5). For both 2'-O-Me and RNA 1.9 equivalents of phosphoramidite were used with an 8:1 ratio of SET:PA. However, a 1× volume phosphoramidite delivery approach was used for all bases.

For both of the above runs, controls were run concomitantly to the experimental runs. Results from small scale deprotection are summarized in Table III ( ) indicates normalized backside. All phosphoramidites used were PAC (phenoxyacetyl) protected. Results for these syntheses are summarized in Table III b.

The term "SET" as used herein refers to S-ethyl tetrazole activator.

The terms "iBuG" and "BzA" as used herein refers to isobutyryl G phosphoramidite and benzoyl A phosphoramidite respectively.

The term "PAC" as used herein refers to phenoxyacetyl protection of exocyclic amine functions.

The term "2'-O-Me" as used herein refers to 2'-O-methyl-ribonucleosides

The term "RNA" as used herein refers to a molecule comprising at least one ribonucleotide residue. By "ribonucleotide" or "2'-OH" is meant a nucleotide with a hydroxyl group at the 2' position of a β-D-ribo-furanose moiety.

The term "port 4/valve 5" as used herein refers to instrument ports and valves on the Pharmacia Oligo Pilot II synthesizer.

The term "CGE FLP" as used herein refers to capillary gel eletrophoresis determined % full length product.

The term "CGE Backside (n+1)" as used herein refers to capillary gel eletrophoresis determined % backside impurity.

The term "CGE Frontside (n−1)" as used herein refers to capillary gel eletrophoresis determined % frontside impurity.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations that is not specifically disclosed herein. Thus, for example, in each instance herein any of the terms "comprising", "consisting essentially of" and "consisting of" can be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed can be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group. Other embodiments are within the following claims.

TABLE I

| Reagent | Equivalents | Amount | Wait Time* DNA | Wait Time* 2'-O-methyl | Wait Time* RNA |
|---|---|---|---|---|---|
| A. 2.5 µmol Synthesis Cycle ABI 394 Instrument | | | | | |
| Phosphoramidites | 6.5 | 163 µL | 45 sec | 2.5 min | 7.5 min |
| S-Ethyl Tetrazole | 23.8 | 238 µL | 45 sec | 2.5 min | 7.5 min |
| Acetic Anhydride | 100 | 233 µL | 5 sec | 5 sec | 5 sec |
| N-Methyl Imidazole | 186 | 233 µL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 µL | 100 sec | 300 sec | 300 sec |
| Acetonitrile | NA | 6.67 mL | NA | NA | NA |
| B. 0.2 µmol Synthesis Cycle ABI 394 Instrument | | | | | |
| Phosphoramidites | 15 | 31 µL | 45 sec | 233 sec | 465 sec |
| S-Ethyl Tetrazole | 38.7 | 31 µL | 45 sec | 233 min | 465 sec |
| Acetic Anhydride | 655 | 124 µL | 5 sec | 5 sec | 5 sec |
| N-Methyl Imidazole | 1245 | 124 µL | 5 sec | 5 sec | 5 sec |
| TCA | 700 | 732 µL | 10 sec | 10 sec | 10 sec |
| Iodine | 20.6 | 244 µL | 15 sec | 15 sec | 15 sec |
| Beaucage | 7.7 | 232 µL | 100 sec | 300 sec | 300 sec |
| Acetonitrile | NA | 2.64 mL | NA | NA | NA |
| C. 0.2 µmol Synthesis Cycle 96 well Instrument | | | | | |
| Reagent | Equivalents: DNA/ 2'-O-methyl/Ribo | Amount: DNA/ 2'-O-methyl/Ribo | Wait Time* DNA | Wait Time* 2'-O-methyl | Wait Time* Ribo |
| Phosphoramidites | 22/33/66 | 40/60/120 µL | 60 sec | 180 sec | 360 sec |
| S-Ethyl Tetrazole | 70/105/210 | 40/60/120 µL | 60 sec | 180 min | 360 sec |
| Acetic Anhydride | 265/265/265 | 50/50/50 µL | 10 sec | 10 sec | 10 sec |
| N-Methyl Imidazole | 502/502/502 | 50/50/50 µL | 10 sec | 10 sec | 10 sec |
| TCA | 238/475/475 | 250/500/500 µL | 15 sec | 15 sec | 15 sec |
| Iodine | 6.8/6.8/6.8 | 80/80/80 µL | 30 sec | 30 sec | 30 sec |

TABLE I-continued

| | | | | | |
|---|---|---|---|---|---|
| Beaucage | 34/51/51 | 80/120/120 | 100 sec | 200 sec | 200 sec |
| Acetonitrile | NA | 1150/1150/1150 µL | NA | NA | NA |

*Wait time does not include contact time during delivery.

TABLE II

| Step | Reagent | Equivalents* | Reaction Time |
|---|---|---|---|
| Detritylation | Dichloroacetic acid in CH$_2$Cl$_2$ (3% v/v, Burdick & Jackson) | Conductivity feedback, followed by 1.5 CV CH$_3$CN wash and another 1.5 CV detrit solution | N/A |
| Coupling | Nucleoside phosphoramidites | 1.5 for 2'-O-methyl's & 2.1 for RNA/2'-C-allyl | 10 min (2'-O-Methyls) |
| | Activator | 8** | 20 min (ribo & 2'-C-allyl) |
| Sulfurization | 0.5 M Beaucage reagent | 7.5 | 3.0 min Contact time |
| Oxidation | 0.05 M I$_2$ in 90:10 pyridine:water (Burdick & Jackson | 4.0 | 1 min contact time |
| Capping | Cap A: 20% NMI, 80% CH$_3$CN | 6.3 | 0.5 min contact time |
| | Cap B: 20% Ac2O, 30% 2,6-lutidine, 50% CH$_3$CN | 9.0 | |

*Equivalents are based on the moles of CPG-bound 3'-terminal nucleoside.
**Activator equivalents are based on moles of nucleoside phosphoramidite.

TABLE III

Results of incorporating inline mixer.

| Synthesis | CGE FLP | CGE Backside (n + 1) | CGE Frontside (n − 1) |
|---|---|---|---|
| a. | | | |
| 8:1 control | 77.4 | 6.7 (7.97) | 5.0 |
| 8:1 mixer | 81.3 | 6.4 (7.3) | 2.6 |
| 6:1 control | 75.0 | 6.3 (7.75) | 4.5 |
| 6:1 mixer | 81 | 5.7 (6.1) | 2.1 |
| 8:1 mixer(p-50) | 83.5 | 4.1 (4.7) | 2.7 |
| b. | | | |
| Run #1 control (GMP223) | 67.3 | 14.6 (17.8) | 3.7 |
| Run #1 mixer (GMP226) | 72.1 | 11.4 (13.6) | 3.3 |
| Run #2 control (GMP229) | 69.4 | 12.7 (15.5) | 4.4 |
| Run #2 mixer (GMP232) | 77.2 | 7.9 (9.3) | 3.7 |

What is claimed is:

1. A compound of the Formula II:

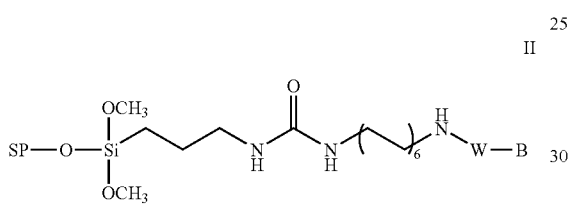

wherein SP is a solid support, W is selected from the group consisting of a carboxy linkage, an amino linkage, a carboxamido linkage, a mercaptoalkyl linkage, a succinyl linkage, an oxalyl linkage, a 3' glycolate termini linkage, an o-nitrophenyl-1,3-propanediol linkage, an alkoxybenzylidene acetal linkage, a hydroquinone-O—O'-diacetic acid linkage, and a pentachlorophenyl-succinate linkage, and B represents a terminal chemical group from which an oligonucleotide can be synthesized.

2. A compound of the Formula VI(a):

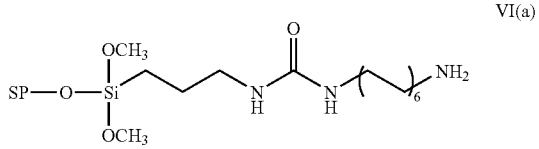

wherein SP is a solid support.

3. The compound of claim 1, wherein said B comprises a nucleic acid, nucleoside, nucleotide, or an abasic moiety.

4. The compound of claim 3, wherein said nucleic acid, nucleoside, nucleotide, or abasic moiety comprises an acid labile protecting group.

5. The compound of claim 4, wherein said acid labile protecting group is a dimethoxytrityl, monomethoxytrityl, or trityl group.

6. A method of synthesizing a compound of claim 1, comprising coupling a terminal chemical group comprising a nucleic acid, nucleoside, nucleotide or an abasic moiety to the primary amine of a compound of Formula VI(a):

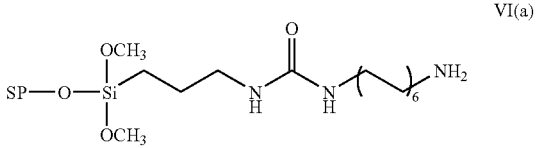

to form said compound of claim 1.

7. The method of claim 6, wherein said coupling is at a loading of about 40 to about 80 μmol/gram of said SP.

8. The method of claim 6, wherein said coupling is at a loading of about 50 to about 60 μmol/gram of said SP.

9. The compound of claim 1, wherein said SP is a controlled pore glass support.

10. The compound of claim 2, wherein said SP is a controlled pore glass support.

11. The compound of claim 1, wherein said W is a succinyl linkage.

12. The compound of claim 2, wherein said W is a succinyl linkage.

13. The compound of claim 11, wherein said B is an abasic moiety.

14. The compound of claim 11, wherein said B is selected from adenosine, cytidine, guanosine, thymidine, or uridine.

15. The compound of claim 13, wherein said abasic succinate is a 5'-O-succinyl-3'-O-DMT deoxyribose.

16. The compound of claim 14, wherein said adenosine succinate is a 5'-O-DMT-3'-O-succinyl adenosine with or without nitrogen protecting groups.

17. The compound of claim 14, wherein said cytidine succinate is a 5'-O-DMT-3'-O-succinyl cytidine with or without nitrogen protecting groups.

18. The compound of claim 14, wherein said guanosine succinate is a 5'-O-DMT-3'-O-succinyl guanosine with or without nitrogen protecting groups.

19. The compound of claim 14, wherein said thymidine succinate is a 5'-O-DMT-3'-O-succinyl thymidine.

20. The compound of claim 14, wherein said uridine succinate is a 5'-O-DMT-3'-O-succinyl uridine.

\* \* \* \* \*